(12) United States Patent
Arakawa et al.

(10) Patent No.: US 11,193,936 B2
(45) Date of Patent: Dec. 7, 2021

(54) METHOD AND REAGENT FOR DETECTING OVARIAN CLEAR CELL ADENOCARCINOMA

(71) Applicants: PUBLIC UNIVERSITY CORPORATION YOKOHAMA CITY UNIVERSITY, Yokohama (JP); TOSOH CORPORATION, Shunan (JP)

(72) Inventors: Noriaki Arakawa, Yokohama (JP); Hisashi Hirano, Yokohama (JP); Etsuko Miyagi, Yokohama (JP); Norihisa Ohtake, Ayase (JP)

(73) Assignees: PUBLIC UNIVERSITY CORPORATION YOKOHAMA CITY UNIVERSITY, Yokohama (JP); TOSOH CORPORATION, Shunan (JP)

( * ) Notice: Subject to any disclaimer, the term of this patent is extended or adjusted under 35 U.S.C. 154(b) by 237 days.

(21) Appl. No.: 16/272,089

(22) Filed: Feb. 11, 2019

(65) Prior Publication Data

US 2019/0170754 A1 Jun. 6, 2019

Related U.S. Application Data

(62) Division of application No. 15/529,550, filed as application No. PCT/JP2015/083272 on Nov. 26, 2015, now abandoned.

(30) Foreign Application Priority Data

Nov. 27, 2014 (JP) .................................. 2014-239433

(51) Int. Cl.
| | |
|---|---|
| *G01N 33/574* | (2006.01) |
| *C07K 16/38* | (2006.01) |
| *C07K 14/47* | (2006.01) |
| *C12N 15/09* | (2006.01) |
| *G01N 27/62* | (2021.01) |
| *C07K 14/81* | (2006.01) |

(52) U.S. Cl.
CPC ....... *G01N 33/57449* (2013.01); *C07K 14/47* (2013.01); *C07K 14/8114* (2013.01); *C07K 16/38* (2013.01); *C12N 15/09* (2013.01); *G01N 27/62* (2013.01); *G01N 33/574* (2013.01); *G01N 2333/8114* (2013.01)

(58) Field of Classification Search
None
See application file for complete search history.

(56) References Cited

U.S. PATENT DOCUMENTS

| 2007/0083334 A1 | 4/2007 | Mintz et al. |
| 2008/0026998 A1 | 1/2008 | Kisiel et al. |
| 2009/0018069 A1 | 1/2009 | Bajaj |
| 2015/0191528 A1 | 7/2015 | Bajaj |

FOREIGN PATENT DOCUMENTS

| JP | 2007506965 A | 3/2007 |
| JP | 2008118915 A | 5/2008 |
| JP | 2013061321 A | 4/2013 |
| JP | 2013063086 A | 4/2013 |
| JP | 2013079979 A | 5/2013 |
| WO | 2005029089 A2 | 3/2005 |
| WO | 2008084219 A1 | 7/2008 |

OTHER PUBLICATIONS

Almagro & Fransson, Frontiers in Bioscience 2008; 13:1619-33 (Year: 2008).*
Arakawa et al. (J. Proteome Res. 2013 12: 4340-4350) (Year: 2013).*
Anderson et al. (J. Proteome Res. 2004 3:234-244) (Year: 2004).*
Williams et al. (Protein Expression and Purification Jan. 30, 2014 96: 14-19) (Year: 2014).*
Santa Cruz Biotechnology, Inc. (TFPI-2 (B-7): sc-48380 Jul. 18, 2012 (Year: 2012).*
International Search Report, issued by International Searching Authority in corresponding International Application No. PCT/JP2015/083272, dated Feb. 23, 2016.
Bützow R., et al., "Purification and Characterization of Placental Protein 5", Biochemical and Biophysical Research Communications, 1988, vol. 150, No. 1, pp. 483-490.
Arakawa N. "Identification and clinical efficacy of novel serum diagnostic marker TFPI-2 for ovarian cancer" Proceedings of the 20th academic meeting of the Japan Society for Proteases in Pathophysiology, Aug. 2015, p. 35.
Chand H.S., et al. "Structure, function and biology of tissue factor pathway inhibitor-2" Thrombosis and Haemostasis, 2005, vol. 94, No. 6, pp. 1122-1130.
Robert C. Bast, Jr., et al. "Reactivity of a Monoclonal Antibody with Human Ovarian Carcinoma" The Journal of Clinical Investigation; The American Society for Clinical Investigation, Inc. vol. 68, 1981 (pp. 1331-1337).

(Continued)

*Primary Examiner* — Peter J Reddig
(74) *Attorney, Agent, or Firm* — Sughrue Mion, PLLC

(57) ABSTRACT

The present invention aims to provide a method for detecting, with high sensitivity and specificity, ovarian clear cell adenocarcinoma, which is highly malignant, among benign and malignant ovarian tumors having various tissue types, and a reagent that can be used for the method. The present invention provides NT-TFPI2, which is a novel processed tissue factor pathway inhibitor 2 polypeptide, as a new detection marker for ovarian clear cell adenocarcinoma. The detection of ovarian clear cell adenocarcinoma is carried out by measuring the amount of NT-TFPI2, or the total amount of NT-TFPI2 and intact TFPI2. The reagent for detecting ovarian clear cell adenocarcinoma contains an antibody that specifically recognizes NT-TFPI2 and intact TFPI2.

4 Claims, 19 Drawing Sheets
(12 of 19 Drawing Sheet(s) Filed in Color)
Specification includes a Sequence Listing.

(56) References Cited

OTHER PUBLICATIONS

Ian Jacobs et al. "The CA 125 tumour-associated antigen: a review of the literature" Human Reproduction vol. 4 No. 1, 1989 (12 pages total).
Daisuke Aoki et al. "Selection and diagnostics use of tumor markers for malignant ovarian tumors" Japan Journal of Molecular Tumor Marker Research vol. 20, 2005; (pp. 98-99).
Yohei Miyagi et al. "cDNA Cloning and mRNA Expression of a Serine Proteinase Inhibitor Secreted by Cancer Cells: Identification as Placental Protein 5 and Tissue Factor Pathway Inhibitor-2" Journal of Biochemistry vol. 116, 1994 (pp. 939-942).
C.N. Rao et al. "HT-1080 Fibrosarcoma Cell Matrix Degradation and Invasion are Inhibited by the Matrix-Associated Serine Protease Inhibitor TPFI-2/33 kDa MSPI" International Journal of Cancer vol. 76, 1998 (pp. 749-756).
M. Ogawa et al. "Paradoxical Discrepancy Between the Serum level and the Placental Intensity of PP5/TFPI-2 in Preeclampsia and/or Intrauterine Growth Restriction: Possible Interaction and Correlation with Glypican-3 Hold the key" Placenta vol. 28, 2007 (pp. 224-232).
Kristen K Zorn et al. "Gene Expression Profiles of Serous, Endometrioid, and Clear Cell Subtypes of Ovarian and Endometrial Cancer" Clinical Cancer Research vol. 11, 2005 (pp. 6422-6430).
Prakasha Kempaiah et al. "Identification of a human TFPI-2 splice variant that is upregulated in human tumor tissues" Molecular Cancer 6:20, 2007 (11 pages total).
Hisashi Takada eta al. "Tissue factor pathway inhibitor 2 (TFPI2) is frequently silenced by aberrant promoter hypermethylation in gastric cancer" Cancer Genetics and Cytogenetics vol. 197, 2010 (pp. 16-24).
Kenji Hibi et al. Methylation of TFPI2 Gene is Frequently Detected in Advanced Well-differentiated Colorectal Cancer Anticancer Research vol. 30, 2010 (pp. 1205-1207).
Qing Zhang et al. "A multiplex methylation-specific PCR assay for the detection of early-stage ovarian cancer using cell-free serum DNA" Gynecologic Oncology vol. 130, 2013 (pp. 132-139).
Cristiana Lo Nigro et al. "Methylated Tissue Factor Pathway Inhibitor 2 (TFPI2) DNA in Serum Is a Biomarker of Metastatic Melanoma" Journal of Investigative Dermatology vol. 133, 2013 (pp. 1278-1285).
Feng-Kai Sun et al. "Detection of TFPI2 Methylation in the Serum of Hepatocellular Carcinoma Patients" Digestive Diseases and Sciences vol. 58, 2013 (pp. 1010-1015).
Noriaki Arakawa et al. "Secretome-Based Identification of TFPI2, A Novel Serum Biomarker for Detection of Ovarian Clear Cell Adenocarcinoma" Journal of Proteome Research vol. 12, 2013 (pp. 4340-4350).
International Preliminary Report on Patentability and translation of Written Opinion issued from the International Bureau in counterpart International Application No. PCT/JP2015/083272, dated Jun. 8, 2017.
Sequence Manipulation Suite (http://bioinfornnatics.org/snns2/protein_nnw.htnnll10/1/2018]) (Year: 2018).

* cited by examiner

1: Secretory TFPI2 culture supernatant 10μL/lane
2: Secretory TFPI2 culture supernatant 3μL/lane
3: Secretory TFPI2 culture supernatant 1μL/lane
4: 293T culture supernatant Fig.8-3
Underline: confidence value of not less than 95
Band A
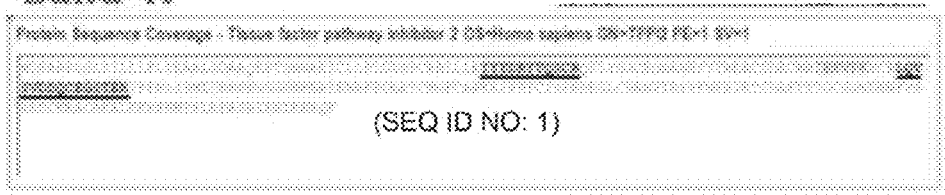
(SEQ ID NO: 1)
Band B
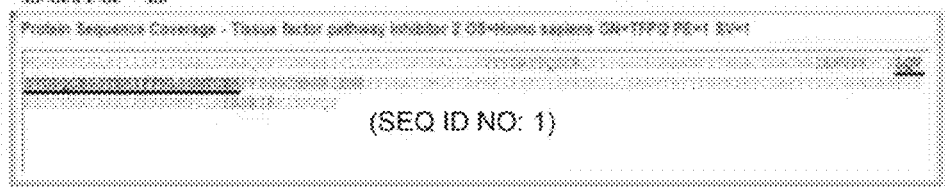
(SEQ ID NO: 1)
Band C
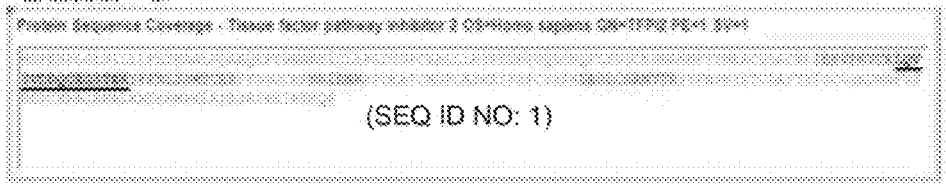
(SEQ ID NO: 1)
Band D
No TFPI2-derived peptide was identified.

Fig.17-1

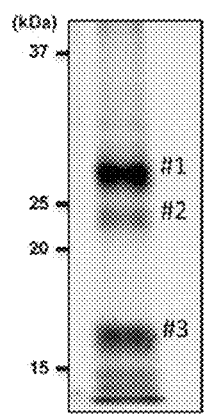

A

B

Band #1, #2

1  MQPARPLGLSILLLFLTEAALGDAAGEPTGRBAEICLLPLDYGPCRALLLRTYYDRYTQSCRQFLYGGCEGHARDFYTWE

81  ACEDACWRIERVPKVCRLQVSVDDQCEGSTEKYFFLSSMTCERFFSGCDRNRIEDRFPDEATCMGFCAPRKIPSFCYS

161  PKDEGLCSANVTRYYFNFRYRTCDAFTYTGCGGBDNNFVSREDCKRACAKAIKKKKMPKLRFASRIRKIRKKQF (SEQ ID NO: 1)

Band #3

1  MQPARPLGLSILLLFLTEAALGDAAGEPTGRBAEICLLPLDYGPCRALLLRTYYDRYTQSCRQFLYGGCEGHARDFYTWE

81  ACEDACWRIERVPKVCRLQVSVDDQCEGSTEKYFFLSSMTCERFFSGCDRNRIEDRFPDEATCMGFCAPRKIPSFCYS

161  PKDEGLCSANVTRYYFNFRYRTCDAFTYTGCGGBDNNFVSREDCKRACAKAIKKKKMPKLRFASRIRKIRKKQF (SEQ ID NO: 1)

—— Peptide in which the O¹⁸ label is detected at C-terminus
——▶ Peptide in which the O¹⁸ label is not detected at C-terminus Fig.17-2
C
DAAQEFTGNNAE (SEQ ID NO: 13)
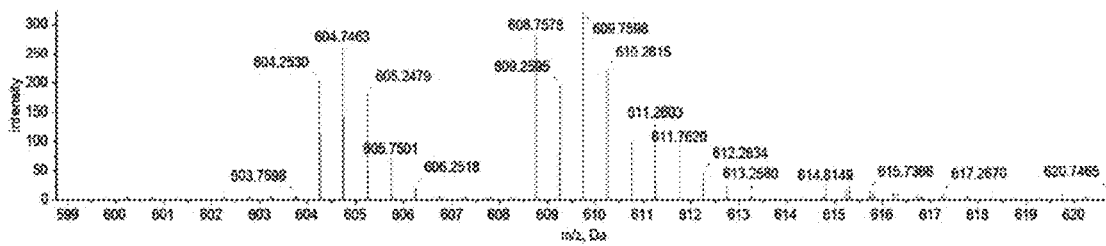
AC[CAM]DDAC[CAM]WRIE (SEQ ID NO: 14)
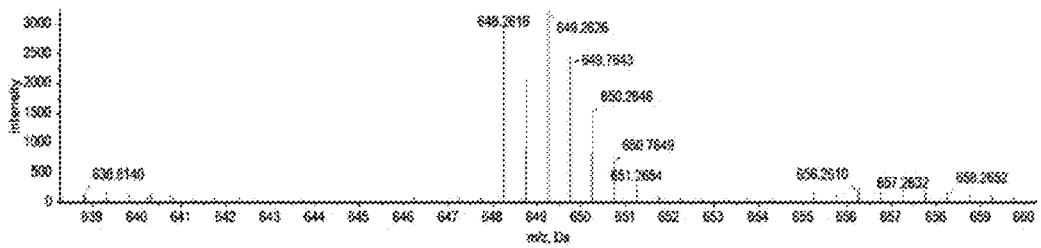
KFFSGGC[CAM]H (SEQ ID NO: 15)
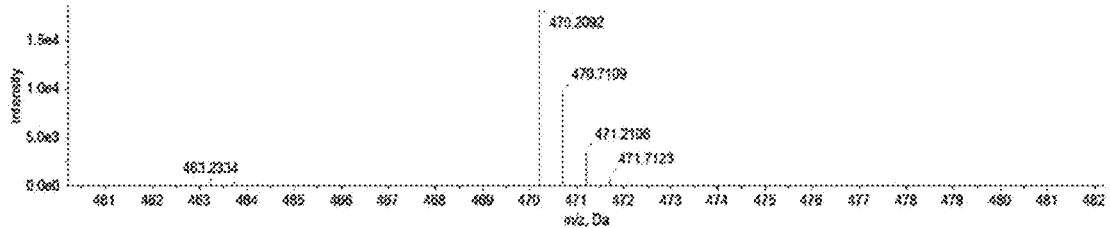
KFFSGGC[CAM] (SEQ ID NO: 16)
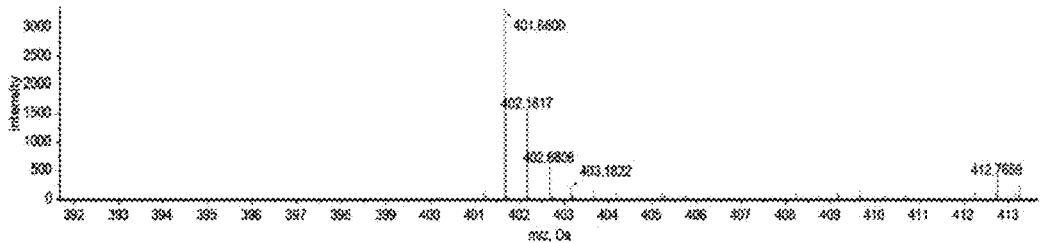
DC[CAM]KRAC[CAM]AKALK (SEQ ID NO: 17)
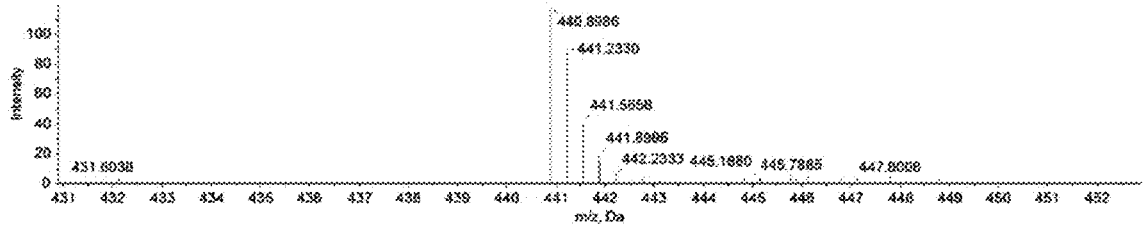

SEQUENCE LISTING

```
<160> NUMBER OF SEQ ID NOS: 17

<210> SEQ ID NO 1
<211> LENGTH: 235
<212> TYPE: PRT
<213> ORGANISM: Homo Sapiens

<400> SEQUENCE: 1

Met Asp Pro Ala Arg Pro Leu Gly Leu Ser Ile Leu Leu Leu Phe Leu
1               5                   10                  15

Thr Glu Ala Ala Leu Gly Asp Ala Ala Gln Glu Pro Thr Gly Asn Asn
            20                  25                  30

Ala Glu Ile Cys Leu Leu Pro Leu Asp Tyr Gly Pro Cys Arg Ala Leu
        35                  40                  45

Leu Leu Arg Tyr Tyr Tyr Asp Arg Tyr Thr Gln Ser Cys Arg Gln Phe
    50                  55                  60

Leu Tyr Gly Gly Cys Glu Gly Asn Ala Asn Asn Phe Tyr Thr Trp Glu
65                  70                  75                  80
```

```
Ala Cys Asp Asp Ala Cys Trp Arg Ile Glu Lys Val Pro Lys Val Cys
            85                  90                  95

Arg Leu Gln Val Ser Val Asp Asp Gln Cys Glu Gly Ser Thr Glu Lys
        100                 105                 110

Tyr Phe Phe Asn Leu Ser Ser Met Thr Cys Glu Lys Phe Phe Ser Gly
        115                 120                 125

Gly Cys His Arg Asn Arg Ile Glu Asn Arg Phe Pro Asp Glu Ala Thr
    130                 135                 140

Cys Met Gly Phe Cys Ala Pro Lys Lys Ile Pro Ser Phe Cys Tyr Ser
145                 150                 155                 160

Pro Lys Asp Glu Gly Leu Cys Ser Ala Asn Val Thr Arg Tyr Tyr Phe
                165                 170                 175

Asn Pro Arg Tyr Arg Thr Cys Asp Ala Phe Thr Tyr Thr Gly Cys Gly
                180                 185                 190

Gly Asn Asp Asn Asn Phe Val Ser Arg Glu Asp Cys Lys Arg Ala Cys
            195                 200                 205

Ala Lys Ala Leu Lys Lys Lys Lys Met Pro Lys Leu Arg Phe Ala
    210                 215                 220

Ser Arg Ile Arg Lys Ile Arg Lys Lys Gln Phe
225                 230                 235

<210> SEQ ID NO 2
<211> LENGTH: 31
<212> TYPE: DNA
<213> ORGANISM: Artificial Sequence
<220> FEATURE:
<223> OTHER INFORMATION: Synthetic Forward primer for GPI-anchor Type
      TFPI2 Expression Plasmid

<400> SEQUENCE: 2
cgatgacgac aagcttgctc aggagccaac a                              31

<210> SEQ ID NO 3
<211> LENGTH: 31
<212> TYPE: DNA
<213> ORGANISM: Artificial Sequence
<220> FEATURE:
<223> OTHER INFORMATION: Synthetic Reverse primer for GPI-anchor Type
      TFPI2 Expression Plasmid

<400> SEQUENCE: 3
catcagtggt gaattcaaat tgcttcttcc g                              31

<210> SEQ ID NO 4
<211> LENGTH: 31
<212> TYPE: DNA
<213> ORGANISM: Artificial Sequence
<220> FEATURE:
<223> OTHER INFORMATION: Synthetic forward primer for Secretory TFPI2
      Expression Plasmid

<400> SEQUENCE: 4
cgatgacgac aagcttgctc aggagccaac a                              31

<210> SEQ ID NO 5
<211> LENGTH: 60
<212> TYPE: DNA
<213> ORGANISM: Artificial Sequence
<220> FEATURE:
<223> OTHER INFORMATION: Synthetic reverse primer for Secretory TFPI2
      Expression Plasmid
```

```
<400> SEQUENCE: 5
agcatcagtg gtgaattctc attagtggcg acgcagaact ttgcaaaatt gcttcttccg    60

<210> SEQ ID NO 6
<211> LENGTH: 31
<212> TYPE: DNA
<213> ORGANISM: Artificial Sequence
<220> FEATURE:
<223> OTHER INFORMATION: Synthetic forward primer for GPI-anchor Type
      TFPI2-KD1

<400> SEQUENCE: 6
cgatgacgac aagcttgctc aggagccaac a                                   31

<210> SEQ ID NO 7
<211> LENGTH: 31
<212> TYPE: DNA
<213> ORGANISM: Artificial Sequence
<220> FEATURE:
<223> OTHER INFORMATION: Synthetic reverse primer for GPI-anchor Type
      TFPI2-KD1

<400> SEQUENCE: 7
catcagtggt gaattctttt tctatcctcc a                                   31

<210> SEQ ID NO 8
<211> LENGTH: 31
<212> TYPE: DNA
<213> ORGANISM: Artificial Sequence
<220> FEATURE:
<223> OTHER INFORMATION: Forward primer for GPI-anchor Type TFPI2-KD2

<400> SEQUENCE: 8
cgatgacgac aagcttgttc ccaaagtttg c                                   31

<210> SEQ ID NO 9
<211> LENGTH: 31
<212> TYPE: DNA
<213> ORGANISM: Artificial Sequence
<220> FEATURE:
<223> OTHER INFORMATION: Reverse primer for GPI-anchor Type TFPI2-KD2

<400> SEQUENCE: 9
catcagtggt gaattctttc tttggtgcgc a                                   31

<210> SEQ ID NO 10
<211> LENGTH: 31
<212> TYPE: DNA
<213> ORGANISM: Artificial Sequence
<220> FEATURE:
<223> OTHER INFORMATION: Forward primer for GPI-anchor Type TFPI2-KD3

<400> SEQUENCE: 10
cgatgacgac aagcttattc catcattttg c                                   31

<210> SEQ ID NO 11
<211> LENGTH: 31
<212> TYPE: DNA
<213> ORGANISM: Artificial Sequence
<220> FEATURE:
<223> OTHER INFORMATION: Reverse primer for GPI-anchor Type TFPI2-KD3

<400> SEQUENCE: 11
catcagtggt gaattcaaat tgcttcttcc g                                   31
```

```
<210> SEQ ID NO 12
<211> LENGTH: 7
<212> TYPE: PRT
<213> ORGANISM: Homo sapiens

<400> SEQUENCE: 12

Phe Phe Ser Gly Gly Cys His
1               5

<210> SEQ ID NO 13
<211> LENGTH: 12
<212> TYPE: PRT
<213> ORGANISM: Homo sapiens

<400> SEQUENCE: 13

Asp Ala Ala Gln Glu Pro Thr Gly Asn Asn Ala Glu
1               5                   10

<210> SEQ ID NO 14
<211> LENGTH: 10
<212> TYPE: PRT
<213> ORGANISM: Homo sapiens

<400> SEQUENCE: 14

Ala Cys Asp Asp Ala Cys Trp Arg Ile Glu
1               5                   10

<210> SEQ ID NO 15
<211> LENGTH: 8
<212> TYPE: PRT
<213> ORGANISM: Homo sapiens

<400> SEQUENCE: 15

Lys Phe Phe Ser Gly Gly Cys His
1               5

<210> SEQ ID NO 16
<211> LENGTH: 7
<212> TYPE: PRT
<213> ORGANISM: Homo sapiens

<400> SEQUENCE: 16

Lys Phe Phe Ser Gly Gly Cys
1               5

<210> SEQ ID NO 17
<211> LENGTH: 11
<212> TYPE: PRT
<213> ORGANISM: Homo sapiens

<400> SEQUENCE: 17

Asp Cys Lys Arg Ala Cys Ala Lys Ala Leu Lys
1               5                   10
```

METHOD AND REAGENT FOR DETECTING OVARIAN CLEAR CELL ADENOCARCINOMA

CROSS REFERENCE TO RELATED APPLICATIONS

This application divisional of U.S. application Ser. No. 15/529,550, filed May 25, 2017, now abandoned, which is a National Stage of International Application No. PCT/JP2015/083272 filed Nov. 26, 2015, claiming priority based on Japanese Patent Application No. 2014-239433 filed Nov. 27, 2014, the contents of all of which are incorporated herein by reference in their entirety.

TECHNICAL FIELD

The present invention relates to a novel processed polypeptide of tissue factor pathway inhibitor 2 (TFPI2) protein (hereinafter referred to as "NT-TFPI2") to be used for detection of ovarian clear cell adenocarcinoma, which is highly malignant among ovarian tumors, and a method for detecting ovarian clear cell adenocarcinoma based on measurement of NT-TFPI2. More specifically, the present invention relates to a method for detecting ovarian clear cell adenocarcinoma using a measurement method in which the total amount of NT-TFPI2 and intact TFPI2 is calculated, and a reagent for detecting ovarian clear cell adenocarcinoma.

BACKGROUND ART

Ovarian cancer is the tumor with the highest mortality rate among gynecological malignancies. In Japan, its annual incidence is about 7,000 to 8,000, and its annual mortality is about 4,000. These numbers are expected to increase year by year. Ovarian surface epithelial malignant tumors account for about 85% of ovarian cancers, and are classified based on their tissue types into the serous type, endometrioid type, mucinous type, clear cell type, and undifferentiated type. In particular, it has been reported that, while the incidence rate of clear cell adenocarcinoma is about 5% in Europeans and Americans, it tends to be high in Japanese with an incidence rate of 20% to 30%. Ovarian clear cell adenocarcinoma is characterized in that Stage I cases account for about half of all cases, often become resistant to chemotherapy using cisplatin, paclitaxel, or the like, and that its malignancy is extremely high.

Conventionally, transvaginal ultrasound, CT, MRI, and the like have been used as methods for detection of ovarian cancer.

As methods for detecting ovarian cancer using a blood component such as whole blood, blood cells, serum, or plasma, methods in which cancer antigen 125 (CA125) is detected are generally known. CA125 is an antigen which is recognized by a monoclonal antibody (OC125) established by Bast et al. in 1981 using a human ovarian cancer cell line (OVCA433) as an immunogen. In cases where CA125 is detected in a blood component, the presence of ovarian surface epithelial ovarian cancer is suggested with a high positive rate. Therefore, the CA125 is widely used for diagnosis including screening of ovarian cancer, evaluation of therapeutic effects on ovarian cancer, and follow-up after therapy (Non-patent Documents 1 and 2).

However, the positive rate of CA125 in ovarian cancer is generally about 80%, and false-negative results are obtained in some cases. Thus, judgment by CA125 is impossible in about 20% of ovarian cancer. Based on comparison among different tissue types of malignant ovarian cancer, the CA125 positive rate in serous type cancer is not less than 90%, while the CA125 positive rate in clear cell adenocarcinoma is about 65%, which is extremely low (Non-patent Document 3). CA125 is also utilized as an auxiliary marker for endometriosis, which is a benign tumor, but CA125 cannot clearly distinguish between benign ovarian tumors and malignant ovarian tumors, and identification of the tissue types of malignant tumors is difficult therewith.

If ovarian clear cell adenocarcinoma, which is highly malignant, can be specifically identified among ovarian tumors having various tissue types by a blood test, the identification may contribute to improvement of the accuracy of diagnosis in screening and follow-up of ovarian cancer, as well as to future development of preoperative treatment methods such as preoperative chemotherapy specific to clear cell adenocarcinoma. Moreover, a canceration theory has been proposed in which the origin of development of ovarian clear cell adenocarcinoma is ovarian endometriosis. Thus, for use in follow-up of ovarian endometriosis and for elucidation of the mechanism of development of the cancer, identification of a specific marker molecule to ovarian clear cell adenocarcinoma and development of a method for detecting this molecule have been demanded.

Tissue factor pathway inhibitor 2 (TFPI2) is the same protein as placental protein 5 (PP5), and is a placenta-derived serine protease inhibitor having three Kunitz-type protease inhibitor domains (Non-patent Document 4). TFPI2 has disulfide bonds at three positions in each Kunitz domain (KD), and it is reported that a plurality of types of TFPI2 are fractionated near a molecular weight of about 30,000 Da to 35,000 Da depending on the asparagine-linked sugar chain structures added to the Kunitz domains 2 and 3 (Non-patent Document 5).

In terms of association of TFPI2 with gynecological diseases, findings such as an increased blood level of TFPI2 in preeclampsia relative to intrauterine growth retardation (IUGR) or normal pregnancy (Non-patent Document 6) and an increased blood level of TFPI2 in patients with endometriosis (Patent Document 1) have been reported. In terms of association with cancer, gene-level studies have been intensively carried out, and it has been reported that TFPI2 is included in a group that shows more than a certain level of gene expression in clear cell adenocarcinoma in uterine cancer and ovarian cancer (Non-patent Document 7), that the gene expression of TFPI2 increases in gastric cancer (Patent Document 2), and that the gene expression of as TFPI2, which is a splicing variant of TFPI2, increases in cancer (Non-patent Document 8). Moreover, since hypermethylation of a CpG island in the TFPI2 promoter region occurs in various cancers, studies on epigenetic markers have been intensively carried out in recent years (Patent Document 3, Non-patent Documents 9, 10, 11, 12, and 13).

On the other hand, the present inventors, Arakawa et al., elucidated that TFPI2 is specifically produced from the clear cell adenocarcinoma cell line of ovarian cancer, and that an increased gene expression of TFPI2 in an ovarian cancer patient tissue specifically occurs only in patients with clear cell adenocarcinoma (Patent Document 4). The inventors also discovered that blood TFPI2 is significantly increased in clear cell adenocarcinoma relative to healthy individuals and cases of endometriosis (Patent Document 5, Non-patent Document 14).

However, the presence of the processed TFPI2 polypeptide has not been known to date. Furthermore, detection of ovarian clear cell adenocarcinoma by measurement of the processed polypeptide, and the effect of the processed polypeptide detection, have of course been unknown.

PRIOR ART DOCUMENTS

Patent Documents

Patent Document 1: Japanese Translated PCT Patent Application Laid-open No. 2007-506965
Patent Document 2: JP 2008-118915 A
Patent Document 3: WO 2008/084219
Patent Document 4: JP 2013-79979 A
Patent Document 5: JP 2013-61321 A Non-Patent Documents Non-patent Document 1: J. Clin. Invest., 68, 1331 (1981)
Non-patent Document 2: Human Reproduction, 4, 1(1989)
Non-patent Document 3: Molecular Tumor Marker Research, 20, 98 (2005)
Non-patent Document 4: J. Biochem., 116, 939 (1994)
Non-patent Document 5: Int. J. Cancer. May 29; 76(5): 749-56 (1998)
Non-patent Document 6: Placenta, 28, 224 (2007)
Non-patent Document 7: Clin. Cancer Res., 11, 6422 (2005)
Non-patent Document 8: Mol. Cancer. March 12; 6: 20. (2007)
Non-patent Document 9: Cancer Genet. Cytogenet., 197, 16 (2010)
Non-patent Document 10: Anticancer Res., 30, 1205 (2010)
Non-patent Document 11: Gynecol. Oncol., 130(i): 132-9 (2013)
Non-patent Document 12: J. Invest. Dermatol., 133(5): 1278-85 (2013)
Non-patent Document 13: Dig. Dis. Sci., 58(4): 1010-5 (2013)
Non-patent Document 14: J. Proteome Res., 2013, 12 (10), pp. 4340-4350

SUMMARY OF THE INVENTION

Problems to be Solved by the Invention

An object of the present invention is to provide a method for detecting ovarian clear cell adenocarcinoma which is highly malignant, with high sensitivity and specificity, among benign and malignant ovarian tumors having various tissue types, and a reagent that can be used for the method.

Means for Solving the Problems

Therefore, the present inventors intensively generated antibodies that show high affinity to the recombinant TFPI2 protein derived from mammalian cells and TFPI2 protein derived from cancer cells, and analysis of properties of these antibodies was carried out. As a result, the present inventors discovered that intact TFPI2 and a novel processed TFPI2 polypeptide (NT-TFPI2) are present in the culture supernatant of clear cell adenocarcinoma cells. The present inventors also discovered that, when intact TFPI2 and NT-TFPI2 are measured using an antibody that recognizes Kunitz domain 1 of TFPI2 in ovarian tumor and uterine tumor, a higher detection specificity for ovarian clear cell adenocarcinoma can be obtained compared to cases where intact TFPI2 alone is measured, so that NT-TFPI2 can be a detection marker for ovarian clear cell adenocarcinoma, thereby completing the present invention.

That is, the present invention includes the following embodiments.
(1) A processed tissue factor pathway inhibitor 2 (TFPI2) polypeptide having the following properties (i) to (iii):
(i) a polypeptide having the amino acid sequence from the 23th residue aspartic acid to the 131st residue histidine or to the 130th residue cysteine in the TFPI2 amino acid sequence of SEQ ID NO:1, or a sequence having an identity of not less than 80% to this sequence;
(ii) a polypeptide that is fractionated into a molecular weight of about 16,000 by reducing SDS-PAGE; and
(iii) a polypeptide whose peptide fragment obtained after asparagine-linked sugar chain cleavage treatment is fractionated into a molecular weight of about 12,000 by reducing SDS-PAGE.
(2) A method for detecting ovarian clear cell adenocarcinoma, the method comprising measuring the amount of the processed TFPI2 polypeptide according to (1) in a sample.
(3) The method according to (2), further comprising measuring the amount of intact TFPI2 in the sample.
(4) The method according to (3), wherein ovarian clear cell adenocarcinoma is judged to be detected in cases where the total of the amount of the processed TFPI2 polypeptide and the amount of intact TFPI2 exceeds a reference value calculated from a control.
(5) The method according to any one of (2) to (4), wherein the measurement is carried out by antigen-antibody reaction using an antibody that binds to an antigenic determinant in the region from the 23th residue aspartic acid to the 131st residue histidine or to the 130th residue cysteine in the TFPI2 amino acid sequence of SEQ ID NO:1.
(6) The method according to (5), wherein the antibody is an antibody that recognizes Kunitz domain 1 of TFPI2.
(7) The method according to any one of (2) to (4), wherein the measurement is carried out using mass spectrometry.
(8) A reagent for detecting ovarian clear cell adenocarcinoma, comprising an antibody that binds to an antigenic determinant in the region from the 23th residue aspartic acid to the 131st residue histidine or to the 130th residue cysteine in the TFPI2 amino acid sequence of SEQ ID NO:1.

Effect of the Invention

The present invention provides a novel detection marker for ovarian clear cell adenocarcinoma. The present invention also provides a method in which ovarian clear cell adenocarcinoma, which is highly malignant, is detected as being positive with high sensitivity and specificity among benign ovarian tumors and malignant ovarian tumors having various tissue types, while benign ovarian tumors and malignant ovarian tumors other than clear cell adenocarcinoma are detected as being negative.

BRIEF DESCRIPTION OF THE DRAWINGS

The application file contains at least one drawing executed in color. Copies of this application publication with the color drawings will be provided by the Office upon request and payment of the necessary fee.

FIG. 8-1 is a diagram (WB images) showing the results of IP-WB analysis of three kinds of monoclonal antibodies using culture supernatants of two kinds of ovarian cancer cells.

FIG. 8-2 is a diagram (Ruby-stained image) (photograph) showing the results of IP-WB analysis of three kinds of monoclonal antibodies using culture supernatants of two kinds of ovarian cancer cells.

FIG. 8-3 is a diagram showing the results of amino acid sequence analysis of IP products obtained with three kinds of monoclonal antibodies using culture supernatants of two kinds of ovarian cancer cells.

FIG. 10-1 is a diagram showing the results of AIA analysis of culture supernatants of three kinds of ovarian cancer obtained with or without N-type sugar chain digestion treatment.

FIG. 10-2 is a diagram showing the recovery rate after immunoprecipitation of culture supernatants of three kinds of ovarian cancer with or without N-type sugar chain digestion treatment.

FIG. 10-3 is a diagram showing WB images of culture supernatants of three kinds of ovarian cancer obtained with or without N-type sugar chain digestion treatment.

FIG. 11-1 is a diagram showing the results of AIA analysis of changes in TFPI2 over time in culture supernatants of two kinds of ovarian cancer.

FIG. 11-2 is a diagram (photographs) showing the results of IP-WB analysis on changes in TFPI2 over time in culture supernatants of two kinds of ovarian cancer.

FIG. 12-1 is a diagram showing the results of AIA analysis of TFPI2 in five kinds of ovarian cancer cells.

FIG. 12-2 is a diagram (photographs) showing the results of IP-WB analysis of TFPI2 in five kinds of ovarian cancer cells.

FIG. 17-1 is a diagram showing the results of analysis of the C-terminal sequence of the NT-TFPI2 polypeptide. A: A SYPRO-Ruby-stained image (photograph) of the antibody column-bound fraction; B: Results of mapping of the sequence information identified from Bands #1 to #3 on the TFPI2 amino acid sequence.

FIG. 17-2 is a diagram showing the results of analysis of the C-terminal sequence of the NT-TFPI2 polypeptide. C: Mass spectrum charts of precursor ions of representative TFPI2-derived peptides detected from Band #3.

MODE FOR CARRYING OUT THE INVENTION

Figure 1:
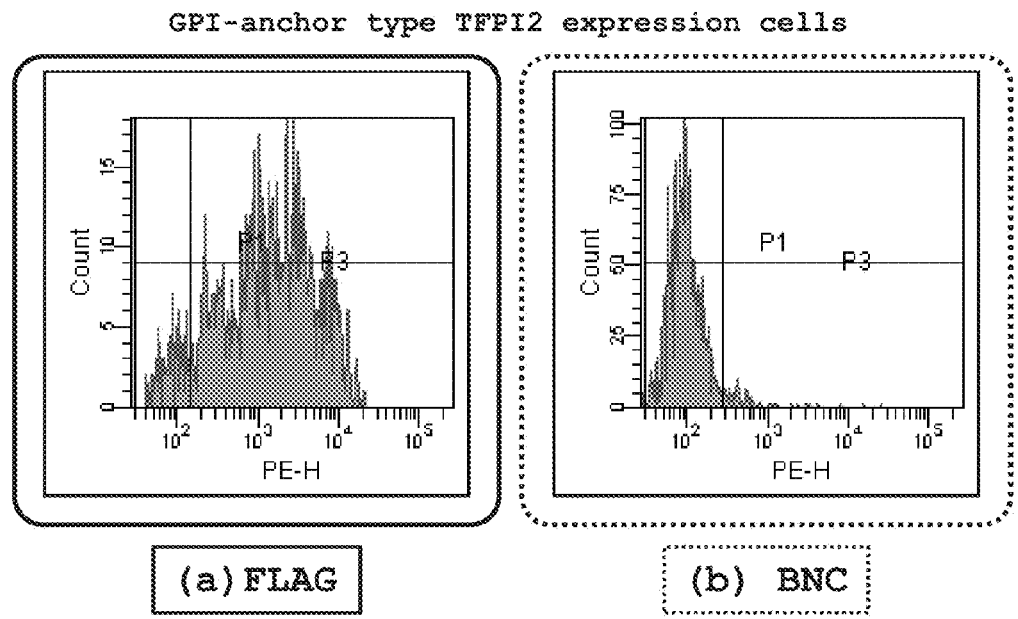
FIG. 1 is a diagram showing the results of FACS analysis of cells to which a GPI-anchor type TFPI2 expression plasmid was introduced, wherein the analysis was carried out using (a) an anti-FLAG antibody or (b) an anti-BNC antibody as a negative control.

<1> Processed Tissue Factor Pathway Inhibitor 2 (TFPI2) Polypeptide of Present Invention The polypeptide of the present invention is a processed tissue factor pathway inhibitor 2 (TFPI2) polypeptide.

As shown in the later-described Examples, NT-TFPI2 was not present in the intracellular fraction of cancer cells, and was present only in the cell culture supernatant. Thus, NT-TFPI2 is assumed to be a fragment polypeptide of TFPI2 that appears through a process in which intact TFPI2 is secreted to the outside of cancer cells, and the secreted intact TFPI2 is localized in the extracellular matrix, followed by undergoing certain characteristic processing.

NT-TFPI2 is a fragment containing Kunitz domain 1, which is positioned in the N-terminal side of intact TFPI2. More specifically, SEQ ID NO:1 is an amino acid sequence based on cDNA of human TFPI2, and the region from the initiating methionine to the 22nd residue glycine corresponds to a signal peptide. NT-TFPI2 has at least the sequence from the 23th residue aspartic acid to the 131st residue histidine or to the 130th residue cysteine, which is a sequence that follows the above region, or an amino acid sequence having an identity of not less than 80% to the sequence. The identity is preferably not less than 90%, more preferably not less than 95%. The polypeptide of the present invention may be a polypeptide having a sequence which is the same as the above sequence except that one or several amino acids are deleted, substituted, inserted, and/or added. The term "several" means preferably 2 to 20, more preferably 2 to 10, still more preferably 2 to 5.

NT-TFPI2 may also have an amino acid sequence located in the C-terminal side of the region from the 23th residue aspartic acid to the 131st residue histidine or to the 130th residue cysteine in the TFPI2 amino acid sequence of SEQ ID NO:1. For example, NT-TFPI2 containing histidine as the 131st amino acid or arginine as the 132nd amino acid is also preferred. NT-TPI2 preferably does not contain the Kunitz domain 3 portion of TFPI2.

Although NT-TFPI2 may also have other peptide fragments in both sides of the above sequence, it preferably does not have an antigenic determinant for an antibody that recognizes Kunitz domain 3 of TFPI2.

Intact TFPI2 is a peptide represented by the region from the 23th residue to the 235th residue in the amino acid sequence of SEQ ID NO:1.

NT-TFPI2 is fractionated into a molecular weight of about 16,000 by reducing SDS-PAGE. More specifically, for example, when SDS-PAGE is carried out under reducing conditions according to a conventional method using polyacrylamide gel with a gradient of 10 to 20% by mass, NT-TFPI2 is detected at a position which is slightly shifted to the lower molecular weight side from the position of the band corresponding to a molecular weight of 17,000 as indicated by a molecular weight marker, preferably Full Range Rainbow Molecular Weight Marker (manufactured by GE Healthcare).

In addition, the peptide fragment of NT-TFPI2 obtained after asparagine-linked sugar chain cleavage treatment is fractionated into a molecular weight of about 12,000 by reducing SDS-PAGE. The asparagine-linked sugar chain cleavage treatment can be carried out using N-glycanase or the like. When the resulting polypeptide, from which the asparagine-linked sugar chain is released, is subjected to, for example, SDS-PAGE under reducing conditions according to a conventional method using polyacrylamide gel with a gradient of 10 to 20% by mass, the band of the polypeptide is detected at the position corresponding to a molecular weight of 12,000 as indicated by a molecular weight marker, preferably Full Range Rainbow Molecular Weight Marker (manufactured by GE Healthcare).

In NT-TFPI2, an asparagine-linked sugar chain is attached to the asparagine corresponding to the 116th residue from the N-terminus of the TFPI2 amino acid sequence of SEQ ID NO:1.

<2> Method for Detecting Ovarian Clear Cell Adenocarcinoma of Present Invention

The method for detecting ovarian clear cell adenocarcinoma of the present invention comprises measuring the amount of NT-TFPI2 in a sample. This method is based on the fact that NT-TFPI2 is characteristically extracellularly present in ovarian clear cell adenocarcinoma cells, unlike in other tissue types. As shown by the later-described Examples, by this method, ovarian clear cell adenocarcinoma can be specifically detected with higher sensitivity and specificity compared to cases where a conventionally known tumor marker (CA125) or intact TFPI2 alone is measured.

In the detection method of the present invention, the amount of intact TFPI2 may be measured in addition to the amount of NT-TFPI2. This is because sufficient sensitivity and specificity can be obtained also by carrying out judgment of detection of ovarian clear cell adenocarcinoma based on the total amount of NT-TFPI2 and intact TFPI2 in the sample. This is also because, as described later, the total amount based on the measurement of both of these and the measured amount of intact TFPI2 alone may be used for indirect measurement of the amount of NT-TFPI2 to detect ovarian clear cell adenocarcinoma.

In the detection method of the present invention, the method for measuring the amount of NT-TFPI2 and/or the amount of intact TFPI2 is not limited. Examples of the method include methods utilizing antigen-antibody reaction in which an antibody that recognizes NT-TFPI2 and/or intact TFPI2 is used, and methods utilizing mass spectrometry.

Specific examples of the methods utilizing antigen-antibody reaction in which an antibody that recognizes NT-TFPI2 and/or intact TFPI2 is used include the following.

(a) A competition method using a labeled measuring object and an antibody that recognizes the measuring object, which method utilizes competitive binding of the labeled measuring object and the measuring object contained in the sample to the antibody.

(b) A method using surface plasmon resonance, wherein the sample is brought into contact with a chip on which an antibody that recognizes the measuring object is immobilized, and a signal dependent on binding of the antibody to the measuring object is detected.

(c) A fluorescence polarization immunoassay using an antibody that recognizes a fluorescently labeled measuring object, which immunoassay utilizes the phenomenon that binding of the antibody to the measuring object causes an increase in the degree of fluorescence polarization.

(d) A sandwich method using two kinds of antibodies (one of which is a labeled antibody) that recognize the measuring object at different epitopes, wherein formation of a complex of the three molecules, that is, the two antibodies and the measuring object, is allowed to occur.

(e) A method in which pretreatment is carried out by concentrating the measuring object in the sample using an antibody that recognizes the measuring object, and the polypeptide in the bound protein is detected using a mass spectrometer or the like.

Although the methods (d) and (e) are simple and versatile, the method (d) is more preferred for processing of a large number of samples since the technologies related to the reagents and the devices for this method have been sufficiently established.

Specific examples of the methods for measuring the amount of NT-TFPI2 and/or the amount of intact TFPI2 utilizing antigen-antibody reaction include the following.

(A) A method using an antibody that recognizes both NT-TFPI2 and intact TFPI2, wherein the total amount of NT-TFPI2 and intact TFPI2 is measured (NT+I-TFPI2 assay system). The antibody that recognizes both NT-TFPI2 and intact TFPI2 is preferably an antibody that binds to an antigenic determinant in the region from the 23th residue aspartic acid to the 131st residue histidine or to the 130th residue cysteine in the TFPI2 amino acid sequence represented by SEQ ID NO:1. The antibody is more preferably an antibody having an antigenic determinant in Kunitz domain 1 of TFPI2. In cases where the above-mentioned sandwich method is used in this method, two kinds of antibodies for different epitopes are used as the antibody.

(B) A method using an antibody that does not recognize NT-TFPI2 but recognizes intact TFPI2, wherein the amount intact TFPI2 alone is measured (I-TFPI2 assay system). The antibody that does not recognize NT-TFPI2 but recognizes intact TFPI2 is preferably an antibody having an antigenic determinant in Kunitz domain 3 of TFPI2. In cases where the above-mentioned sandwich method is used in this method, two kinds of antibodies for different epitopes are used as the antibody. At least one of these is an antibody that does not recognize NT-TFPI2 but recognizes intact TFPI2, and the other may be either an antibody that does not recognize NT-TFPI2 but recognizes intact TFPI2, or an antibody that recognizes both NT-TFPI2 and intact TFPI2.

(C) A method in which the amount of intact TFPI2 alone measured in the I-TFPI2 assay system of (B) is subtracted from the total amount of NT-TFPI2 and intact TFPI2 measured in the NT+I-TFPI2 assay system of (A), to calculate the amount of NT-TFPI2 alone.

(D) A method using an antibody that does not recognize intact TFPI2 but recognizes NT-TFPI2, wherein the amount NT-TFPI2 alone is measured. Examples of the antibody that does not recognize intact TFPI2 but recognizes NT-TFPI2 include antibodies that specifically recognize a peptide sequence in the C-terminal portion of NT-TFPI2. For example, in cases where the above-mentioned sandwich method is used, such an antibody is used as the solid-phase antibody, and an antibody having a recognition site in Kunitz domain 1 is used as the detection antibody.

In the method for detecting ovarian clear cell adenocarcinoma of the present invention, the amount of NT-TFPI2 alone measured by the method of (C) or (D) may be used as a criterion. However, sufficient sensitivity and specificity can be obtained also by using the total amount of NT-TFPI2 and intact TFPI2 measured by the method of (A) as a criterion. The latter method is more preferred from the viewpoint of the fact that the antibody can be easily obtained, and that the measurement can be simply carried out by a single step.

The antibody that recognizes NT-TFPI2 and/or intact TFPI2 can be obtained by immunizing an animal using as an immunogen, for example, the NT-TFPI2 polypeptide or the intact TFPI2 protein itself, an oligopeptide composed of a partial region of the NT-TFPI2 polypeptide or the intact TFPI2 protein, or a polynucleotide encoding the intact molecule or a partial region of the NT-TFPI2 polypeptide or of the intact TFPI2 protein.

The animal to be used for the immunization is not limited as long as the animal has ability to produce antibodies. The animal may be a mammal normally used for immunization, such as mouse, rat, or rabbit, or may be a bird such as chicken.

In cases where the NT-TFPI2 polypeptide or the intact TFPI2 protein itself, or an oligopeptide composed of a partial region of the NT-TFPI2 polypeptide or the intact TFPI2 protein is used as an immunogen, its structure may change during the process of preparing the protein or the oligopeptide. Therefore, in some cases, the antibody obtained may not have high specificity or binding capacity to the desired antigen, so that quantification of the concentration of TFPI2 contained in the sample may be inaccurate. On the other hand, in cases where a protein expression vector containing a polynucleotide encoding the intact molecule or a partial region of the NT-TFPI2 polypeptide or of the intact TFPI2 protein is used as an immunogen, the intact molecule or partial region of the NT-TFPI2 polypeptide or of the intact TFPI2 protein introduced is expressed as it is without undergoing a structural change in the body of the immunized animal. Therefore, an antibody having high specificity and binding capacity (that is, high affinity) to the NT-TFPI2 polypeptide or intact TFPI2 in the sample can be obtained, which is preferred.

The antibody that recognizes TFPI2 may be either a monoclonal antibody or a polyclonal antibody. The antibody is preferably a monoclonal antibody.

The method of establishment of a hybridoma cell that produces an antibody that recognizes NT-TFPI2 and/or intact TFPI2 may be appropriately selected from methods whose techniques have been established. For example, a hybridoma cell that produces a monoclonal antibody that recognizes NT-TFPI2 and/or intact TFPI2 can be established by collecting B cells from an animal immunized by the above method, fusing the B cells with myeloma cells electrically or in the presence of polyethylene glycol, selecting a hybridoma cell that produces a desired antibody using HAT medium, and preparing the selected hybridoma cell into a monoclone by the limiting dilution method.

The selection of the antibody that recognizes NT-TFPI2 and/or intact TFPI2, for example, the monoclonal antibody that recognizes NT-TFPI2 and/or intact TFPI2, used in the method for detecting ovarian clear cell adenocarcinoma of the present invention may be carried out based on affinity to GPI (glycosylphosphatidylinositol)-anchor type TFPI2 or secretory TFPI2 derived from a host expression system.

The host is not limited, and may be appropriately selected from microorganism cells such as E. coli or yeast, insect cells, and animal cells that are usually used for protein expression by those skilled in the art. The host is preferably a mammalian cell since it enables expression of a protein having a structure similar to that of natural NT-TFPI2 and/or intact TFPI2 by post-translational modification such as disulfide bonding or glycosylation. Examples of the mammalian cell include the human embryonic kidney (HEK)-derived 293T cell line, monkey kidney COST cell line, Chinese hamster ovary (CHO) cells, and cancer cells isolated from human.

The method of purification of the antibody to be used in the method for detecting ovarian clear cell adenocarcinoma of the present invention may be appropriately selected from methods whose techniques have been established. For example, after culturing hybridoma cells which are established by the above method and which produce an antibody, the culture supernatant may be collected, and the antibody may be concentrated, if necessary, by ammonium sulfate precipitation. Thereafter, by affinity chromatography using a carrier to which Protein A, Protein G, Protein L, or the like is immobilized, and/or by ion-exchange chromatography, purification of the antibody is possible.

The labeled antibody used for the antigen-antibody reaction in the sandwich method described above may be prepared by labeling an antibody purified by the above method with an enzyme such as peroxidase or alkaline phosphatase. The labeling may also be carried out using a method whose technique has been sufficiently established.

The method for measuring the amount of NT-TFPI2 and/or the amount of intact TFPI2 utilizing mass spectrometry in the detection method of the present invention is described below concretely.

In cases of a blood sample, a pretreatment step is preferably carried out by removing proteins contained in large amounts in blood such as albumin, immunoglobulin, and transferrin using Agilent Human 14 or the like, and performing further fractionation by ion exchange, gel filtration, reverse-phase HPLC, and/or the like.

The measurement can be carried out by tandem mass spectrometry (MS/MS), liquid chromatography-tandem mass spectrometry (LC/MS/MS), matrix assisted laser desorption ionization time-of-flight mass spectrometry (MALDI-TOF/MS), surface enhanced laser desorption ionization mass spectrometry (SELDI-MS), or the like.

In the detection method of the present invention, ovarian clear cell adenocarcinoma is preferably judged to be detected when the amount of NT-TFPI2 obtained by the measurement is higher than a reference value (cutoff value) calculated from a control. Alternatively, ovarian clear cell adenocarcinoma is preferably judged to be detected when the total of the amount of NT-TFPI2 and the amount of intact TFPI2 obtained by the measurement is higher than a reference value (cutoff value) calculated from a control.

The amount of NT-TFPI2 and the amount of intact TFPI2 used for the judgment may be either measured values or converted concentration values. The converted concentration value means a value converted from the measured value based on a calibration curve prepared using TFPI2 as a standard sample.

The reference value (cutoff value) may be appropriately set to a measured value which provides optimum sensitivity and specificity, by carrying out measurement for non-clear-cell-adenocarcinoma samples such as non-clear-cell-adenocarcinoma ovarian tumors, uterine tumors, and/or samples from healthy individuals, as well as for clear-cell-adenocarcinoma samples, and then carrying out receiver operating characteristic (ROC) curve analysis. More specifically, for example, in cases where serum is used as the sample, the reference value (cutoff value) of the total of the amount of NT-TFPI2 and the amount of intact TFPI2 may be set to 1.9, which is a measured value (rate:nmol/(L·s)) calculated based on the concentration of 4-methylumbelliferone produced by alkaline phosphatase per unit time.

<3> Reagent for Detecting Ovarian Clear Cell Adenocarcinoma of Present Invention The reagent for detecting ovarian clear cell adenocarcinoma of the present invention comprises an antibody that binds to an antigenic determinant in the region from the 23th residue amino acid to the 131st residue or 130th residue amino acid in the TFPI2 amino acid sequence of SEQ ID NO:1. The antibody is preferably an antibody that recognizes Kunitz domain 1 of TFPI2. The antibody can recognize both NT-TFPI2 and intact TFPI2.

In cases where the reagent of the present invention is used in the sandwich method described above, the reagent preferably contains, as the antibody, two kinds of antibodies for different epitopes.

The reagent for detecting ovarian clear cell adenocarcinoma of the present invention may further contain a reagent for detecting a tumor marker for ovarian cancer containing an antibody that recognizes the tumor marker for ovarian cancer. Examples of the tumor marker for ovarian cancer include CA125.

The antibody contained in the reagent of the present invention may be an antibody itself, a labeled antibody, or an antibody immobilized on a solid phase.

The reagent of the present invention is described below concretely for cases where it is used for a two-step sandwich method, which is one mode of the sandwich method. However, the present invention is not limited thereto.

The reagent of the present invention can be prepared by the method described in the following (I) to (III). (I) First, Antibody 1, one of the two kinds of antibodies for different epitopes that recognize NT-TFPI2 and intact TFPI2 (hereinafter referred to as "Antibody 1" and "Antibody 2"), is bound to a carrier capable of B/F (Bound/Free) separation such as an immunoplate or magnetic particles. The binding method may be either physical binding utilizing hydrophobic boning, or chemical bonding using a linker reagent capable of cross-linking two substances to each other.

(II) After the binding of the Antibody 1 to the carrier, the carrier surface is subjected to blocking treatment using bovine serum albumin, skim milk, a commercially available immunoassay blocking agent, or the like for preventing non-specific binding, to provide a primary reagent.

(III) After labeling the other antibody, Antibody 2, a solution containing the obtained labeled antibody is provided as a secondary reagent. Preferred examples of the substance with which Antibody 2 is labeled include enzymes such as peroxidase and alkaline phosphatase; substances detectable with detection devices, such as fluorescent substances, chemiluminescent substances, and radioisotopes; and substances to which another molecule specifically binds, such as biotin, to which avidin specifically binds. Preferred examples of the solution for the secondary reagent include buffers with which antigen-antibody reaction can be favorably carried out, such as phosphate buffer and Tris-HCl buffer.

The thus prepared reagent of the present invention may be freeze-dried, if necessary.

In cases of a one-step sandwich method, binding of Antibody 1 to the carrier and subsequent blocking treatment may be carried out in the same manner as in (I) and (II) to prepare an antibody-immobilized carrier, and a buffer containing a labeled Antibody 2 may be further added to the antibody-immobilized carrier, to provide a reagent.

For measurement of NT-TFPI2 and intact TFPI2 by a two-step sandwich method using reagents obtained by the method described above, the method described in the following (IV) to (VI) may be carried out.

(IV) The primary reagent prepared in (II) is brought into contact with a sample for a predetermined period of time at a constant temperature. In terms of the reaction conditions, the reaction may be carried out at a temperature within the range of 4° C. to 40° C. for 5 minutes to 180 minutes.

(V) Unreacted substances are removed by B/F separation, and then the secondary reagent prepared in (III) is brought into contact with the resulting reaction product for a predetermined period of time at a constant temperature to allow formation of a sandwich complex. In terms of the reaction conditions, the reaction may be carried out at a temperature within the range of 4° C. to 40° C. for 5 minutes to 180 minutes.

(VI) Unreacted substances are removed by B/F separation, and the labeling substance of the labeled antibody is quantified. Based on a calibration curve prepared using a TFPI2 solution having a known concentration as a standard sample, the concentration of human NT-TFPI2 and intact TFPI2 in the sample is quantified.

The above description on the TFPI2 detection reagent also applies to the reagent for detecting a tumor marker for ovarian cancer. The reagent for detecting a tumor marker for ovarian cancer may be one prepared in the same manner as the reagent of the present invention, or may be a commercially available product.

The amount of each reagent component such as the antibody contained in the detection agent may be appropriately set depending on conditions such as the amount of the sample, the type of the sample, the type of the reagent, and the detection method. More specifically, for example, in cases where the amount of NT-TFPI2 and the amount of intact TFPI2 are measured as described below by a sandwich method using 50 μL of 2.5-fold diluted serum or plasma as a sample, the amount of the antibody to be bound to the carrier may be 100 ng to 1000 μg, and the amount of the labeled antibody may be 2 ng to 20 μg per the reaction system in which 50 μL of the sample is reacted with the antibodies.

The reagent for detecting ovarian clear cell adenocarcinoma of the present invention is applicable to either manual detection or detection using an automatic immunodiagnostic device. Detection using an automatic immunodiagnostic device is especially preferred since it enables the detection without being influenced by endogenous measurement-inhibiting factors and competing enzymes contained in the sample, and also enables rapid quantification of the concentrations of NT-TFPI2 and intact TFPI2, as well as tumor markers for ovarian cancer.

Examples of the sample (test sample) to be subjected to the method for detecting ovarian clear cell adenocarcinoma of the present invention and the detection reagent of the present invention include blood components such as whole blood, blood cells, serum, and plasma; extracts from cells and tissues; urine; and cerebrospinal fluid. Although an ovarian tissue biopsy sample may be subjected to the test, a culture supernatant of the biopsy sample is used as the sample in such cases. A blood component or a body fluid such as urine is preferably used as the sample since it allows simple noninvasive detection of ovarian clear cell adenocarcinoma. From the viewpoint of simplicity of sample collection and versatility for other test items, use of a blood component as the sample is especially preferred. The dilution rate of the sample may be appropriately selected from no dilution to 100-fold dilution depending on the type and the conditions of the sample used. For example, 50 μL of a 2.5-fold diluted sample may be used in cases of serum or plasma.

EXAMPLES

Examples are shown below for concrete description of the present invention. However, these Examples merely show examples of the present invention, and the present invention is not limited by the Examples.

<Example 1> Construction of Vector for DNA Immunization

For efficient induction of humoral immunity by DNA immunization, it is preferred to localize the subject antigen protein on the cell surface as a membrane-bound protein. Since TFPI2 is originally a secretory protein, a plasmid vector that can express a protein in which a GPI (glycosylphosphatidylinositol) anchor is attached to the C-terminal side of TFPI2 (hereinafter referred to as GPI-anchor type TFPI2) was constructed for allowing localization of TFPI2 on the cell surface.

(1) Using the following primers (a), a polynucleotide composed of the 73rd to 705th bases of TFPI2 cDNA (GenBank No. NM_006528) was amplified by RT-PCR according to a conventional method.

(a) Primers for GPI-Anchor Type TFPI2 Expression Plasmid
Forward:
5'-cgatgacgacaagcttgctcaggagccaaca-3' (SEQ ID NO:2; wherein the 15 bases in the 3'-end side correspond to the base sequence from position 73 to position 87 in GenBank No. NM_006528)
Reverse:
5'-catcagtggtgaattcaaattgcttcttccg-3' (SEQ ID NO:3; wherein the 15 bases in the 5'-end side correspond to the base sequence from position 691 to position 705 in GenBank No. NM_006528)

(2) Into the HindIII-EcoRI site of pFLAG1 (manufactured by SIGMA), which contains the coding region for the GPI anchor of placental alkaline phosphatase and the coding region for a FLAG tag, the RT-PCR amplification product obtained in (1) was inserted using In-fusion (manufactured by Clontech) according to its protocol, to construct a GPI-anchor type TFPI2 expression plasmid in which the FLAG tag peptide is attached to the N-terminal side, and the GPI anchor is attached to the C-terminal side.

(3) In order to confirm that TFPI2 expressed by the polynucleotide inserted in the expression plasmid constructed in (2) is localized on the cell surface as assumed, the following test was carried out using the 293T cell line, which is a transiently expressing cell.

(3-1) The GPI-anchor type TFPI2 expression plasmid constructed in (2) was transfected into the 293T cell line according to a conventional method.

(3-2) The transfected 293T cells were cultured in a 5% $CO_2$ incubator using D-MEM medium supplemented with 10% FBS (fetal bovine serum) (manufactured by Wako Pure Chemical Industries, Ltd.) for 24 hours at 37° C., to allow transient expression of TFPI2 protein.

(3-3) To the cultured cells obtained in (3-2), a mouse anti-FLAG M2 antibody manufactured by SIGMA, which specifically binds to the FLAG tag, or a mouse anti-BNC antibody as a negative control, which does not bind to the FLAG tag, was added, and the cells were incubated for 30 minutes. BNC is a peptide composed of seven amino acids in the C-terminal side of BNP (brain natriuretic peptide) (JP 2009-240300 A).

(3-4) Thereafter, a fluorescently labeled anti-mouse IgG antibody (manufactured by BECKMAN COULTER) was added to the cells, and the cells were incubated for 30 minutes, followed by performing FACS (Fluorescence Activated Cell Sorting) analysis.

The results of the FACS analysis are shown in FIG. 1. As a result of the analysis, in the case of the negative control, wherein the anti-BNC antibody was added (FIG. 1(b)), no increase in the signal, that is, no shift, due to fluorescently labeled cells was found. On the other hand, a shift due to fluorescently labeled cells was found in the case where the anti-FLAG antibody was added (FIG. 1(a)). From these results, it was shown that the GPI-anchor type TFPI2 to which the FLAG tag peptide is attached was localized on the cell surface after its protein expression.

<Example 2> Immunization and Blood Collection

Immunization of mice was carried out by administering, to four Balb/c mice, 100 μL of a PBS solution prepared such that the solution contains 40 μg of the GPI-anchor type TFPI2 expression plasmid constructed in Example 1(2) in terms of the amount of DNA. On Day 7, Day 14, Day 21, Day 28, and Day 35 after the first immunization, additional administration was carried out. On Day 42 after the first immunization, blood was collected to prepare antiserum to provide antisera A-1 to A-4.

<Example 3> Preparation of GPI-anchor Type TFPI2 Constantly Expressing Cells

For evaluation of the antisera, a Chinese-hamster-ovary-derived cell line CHO-K1 that can constantly express the GPI-anchor type TFPI2 was prepared by the following method.

(1) The TFPI2 expression plasmid constructed in Example 1 (2) was introduced into the CHO-K1 cell line by gene transfer according to a conventional method. Thereafter, the cells were cultured in a 5% $CO_2$ incubator using Hams F12 medium supplemented with 10% FBS (manufactured by Wako Pure Chemical Industries, Ltd.) for 24 hours at 37° C.

(2) Thereafter, a solution of the antibiotic Geneticin (manufactured by Invitrogen) was added to the culture at 250 μg/mL, and culture was carried out for additional three weeks.

(3) CHO-K1 cells that constantly express the GPI-anchor type TFPI2 were obtained with an anti-FLAG antibody using a cell sorter.

<Example 4> Construction of Secretory TFPI2 Expression Plasmid

In the TFPI2 expression plasmid constructed in Example 1 (2), an oligonucleotide encoding a BNC peptide composed of seven amino acids in the C-terminal side of BNP (brain natriuretic peptide) (Patent Document 5) was further inserted into the position between the inserted TFPI2 gene and the GPI anchor-coding region present in its 3'-end side. By this, a plasmid capable of expressing a secretory TFPI2 having the FLAG peptide in the N-terminal side and the BNC peptide in the C-terminal side, but having no GPI anchor was prepared. The preparation method is described below more concretely.

(1) Using the following primers (b), a polynucleotide in which an oligonucleotide encoding the BNC peptide is added to the 3'-end side of intact TFPI2 cDNA excluding the start codon and the stop codon (the region from position 148 to position 780 in GenBank No. NM_006528) was amplified by RT-PCR according to a conventional method.

(b) Primers for Secretory TFPI2 Expression Plasmid
Forward:
5'-cgatgacgacaagcttgctcaggagccaaca-3' (SEQ ID NO:4; wherein the 15 bases in the 3'-end side correspond to the base sequence from position 73 to position 87 in GenBank No. NM_006528)
Reverse:
5'-agcatcagtggtgaattctcattagtggcgacgcagaactttgcaaaat-tgcttcttccg-3' (SEQ ID NO:5; wherein the 15 bases in the 5'-end side correspond to the base sequence from position 691 to position 705 in GenBank No. NM_006528)
(2) Into the HindIII-EcoRI site of pFLAG1 (manufactured by SIGMA), which is a plasmid containing the GPI anchor region of placental alkaline phosphatase, the RT-PCR amplification product of (1) was inserted using In-fusion (manufactured by Clontech) according to its protocol, to construct a secretory TFPI2 expression plasmid.
(3) In order to confirm that the secretory TFPI2 expressed from the polynucleotide inserted in the pFLAG1 has the FLAG tag in the N-terminal side and the BNC tag in the C-terminal side, the following test was carried out using the 293T cell line, which is a transiently expressing cell.
(3-1) In the same manner as described in Example 1, the secretory TFPI2 expression plasmid constructed in (2) was transfected into the 293T cell line, and secretory TFPI2 protein was transiently expressed. The culture liquid after 72 hours of culture was centrifuged, and the resulting supernatant was collected as a secretory TFPI2 protein solution.
(3-2) Using the secretory TFPI2 protein solution as a sample, (A) an enzyme immunoassay (ELISA) and (B) Western blotting (WB) were carried out.
(A) ELISA
(A-1) A rabbit anti-FLAG polyclonal antibody (manufactured by ROCKLAND) was diluted with carbonate buffer (pH 9.8) such that its amount became 100 ng/well, and then immobilized on a MaxiSorp 96-well plate (manufactured by NUNC).
(A-2) After allowing the reaction to proceed at 4° C. overnight, the plate was washed three times with TBS (Tris-Buffered Saline), and TBS solution supplemented with 3% bovine serum albumin (BSA) was added to each well at 250 µL/well. The plate was incubated at room temperature for 2 hours.
(A-3) The plate was then washed three times with TBS. A secretory TFPI2 protein solution and, as a negative control, a culture supernatant of the 293T cell line which was not transfected TFPI2 expression plasmid were added thereto at 50 µL/well. The plate was incubated at room temperature for 1 hour.
(A-4) After washing the plate three times with TBS supplemented with 0.5% Tween 20 (TBS-T), a mouse anti-BNC monoclonal antibody solution diluted to 1 µg/mL with TBS-T supplemented with 1% BSA (1% BSA/TBS-T) was added to the plate at 50 µL/well. The plate was incubated at room temperature for 1 hour.
(A-5) After washing the plate three times with TBS-T, a horseradish peroxidase (HRP)-labeled anti-mouse immunoglobulin G-Fc antibody (manufactured by SIGMA) solution 10,000-fold diluted with 1% BSA/TBS-T was added to the plate at 50 µL/well, and the plate was incubated at room temperature for 1 hour.
(A-6) After washing the plate four times with TBS-T, TMB Microwell Peroxidase Substrate (manufactured by KPL) was added to the plate, and the reaction was stopped with 1 mol/L phosphoric acid solution, followed by measuring the absorbance at 450 nm using an absorbance measurement plate reader.

Figure 2:
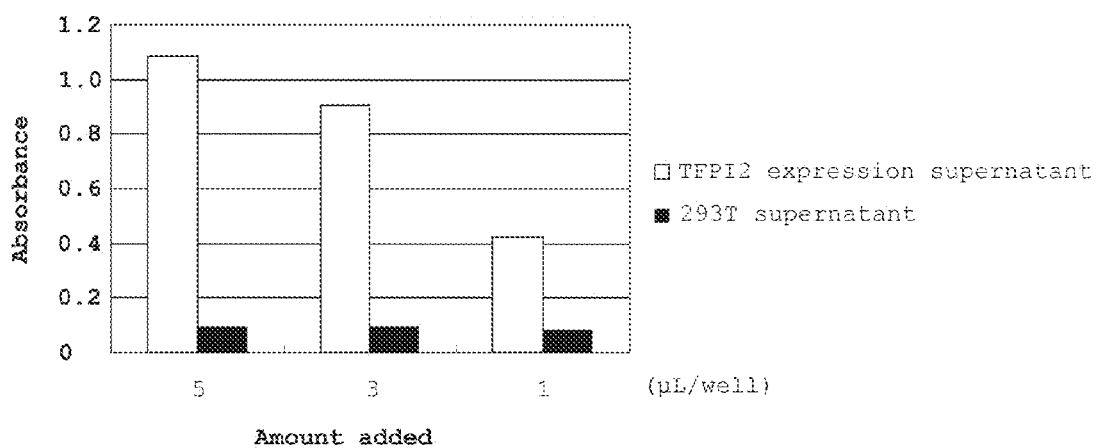
FIG. 2 is a diagram showing the results of ELISA analysis of secretory TFPI2. The ordinate represents the absorbance, and the abscissa represents the amount of each solution added per well.
Figure 3:
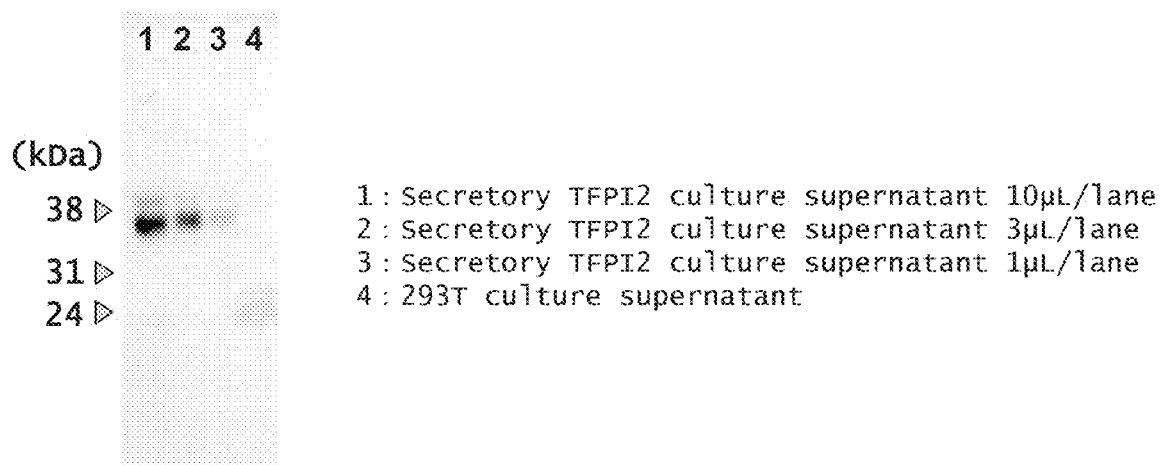
FIG. 3 is a diagram showing the results (a photograph) of Western blotting analysis of secretory TFPI2.

(B) Western Blotting
(B-1) The secretory TFPI2 protein solution obtained in (3-1), and, as a negative control, a culture supernatant of the 293T cell line which was not transfected TFPI2 expression plasmid, were separated by SDS-PAGE, and transferred to a PVDF membrane (manufactured by GE Healthcare).
(B-2) The membrane was blocked by reaction with TBS-T supplemented with 5% skim milk (blocking solution) at room temperature for 2 hours, and an alkaline phosphatase-labeled anti-BNC antibody was added to the blocking solution at 1 µg/sheet, incubated at 4° C. overnight.
(B-3) The membrane was washed with TBS-T, and the obtained chemiluminescence was detected with a photosensitive film using Western Lightning CDP-Star (manufactured by Perkin-Elmer Corp.).
The analysis results obtained by ELISA are shown in FIG. 2. In the case of the secretory TFPI2 protein solution (culture supernatant of secretory TFPI2), clear signals could be observed in a manner dependent on the amount of the sample added, unlike the case of the negative control (culture supernatant of non transfected 293T). Thus, production of the secretory TFPI2 protein into the culture supernatant was shown.
The analysis results obtained by Western blotting are shown in FIG. 3. In the case of the secretory TFPI2 protein solution (culture supernatant of secretory TFPI2), a clear band was detected near a molecular weight of about 35 kDa. Thus, production of secretory TFPI2 protein having the FLAG tag in the N-terminus and the BNC tag in the C-terminus into the culture supernatant was shown.

<Example 5> Evaluation of Mouse Antisera

The mouse antisera collected in Example 2 were analyzed by cell enzyme immunoassay (CELISA) using the GPI-anchor type TFPI2 expression CHO-K1 cells prepared in Example 3, and by ELISA using the secretory TFPI2 protein solution obtained in Example 4. For studying specificity, expression plasmids that express a non-TFPI2 protein as a GPI-anchor type (having a FLAG tag in the N-terminal side and a GPI anchor in the C-terminal side) or as a secretory type (having a FLAG tag in the N-terminal side and a BNC tag in the C-terminal side) were constructed based on a known gene sequence in the same manner as the TFPI2 expression plasmid described above, and the constructed expression plasmids were transfected into the 293T cell line or CHO-K1 cells. The non-TFPI2 protein is hereinafter also referred to as control protein.
(1) CELISA Analysis
(1-1) To a 96-well plate, the GPI-anchor type TFPI2 expression CHO-K1 cells prepared in Example 3, and, as negative control cells, CHO-K1 cells that express the control protein as a GPI-anchor type, were added at $5 \times 10^4$ cell/well, and the cells were cultured in a 5% $CO_2$ incubator using Hams F12 medium supplemented with 10% FBS (manufactured by Wako Pure Chemical Industries, Ltd.) for 24 hours at 37° C.
(1-2) To the GPI-anchor type TFPI2-expressing cells and the negative control cells, each of 2000-fold diluted antisera (A1 to A4) or a mouse anti-FLAG M2 antibody (manufactured by SIGMA) was added as a primary antibody, and the reaction was incubated at room temperature for 1 hour.
(1-3) After the reaction, the plate was washed, and a horseradish peroxidase (HRP)-labeled anti-mouse immunoglobulin G-Fc antibody (manufactured by SIGMA) was added to the plate as a secondary antibody, incubated at room temperature for 1 hour.

(1-4) After the incubation, the plate was washed, and TMB Microwell Peroxidase Substrate (manufactured by KPL) was added to the plate. The reaction was then stopped with 1 mol/L phosphoric acid solution, and the absorbance at 450 nm was measured using an absorbance measurement plate reader.

(2) ELISA Analysis

Each mouse antiserum was evaluated by the same method as in Example 4(A) except that a culture supernatant of the 293T cell line that expresses the control protein as a secretory type (hereinafter also referred to as secretory-type control protein solution) was used as the negative control.

Figure 4:
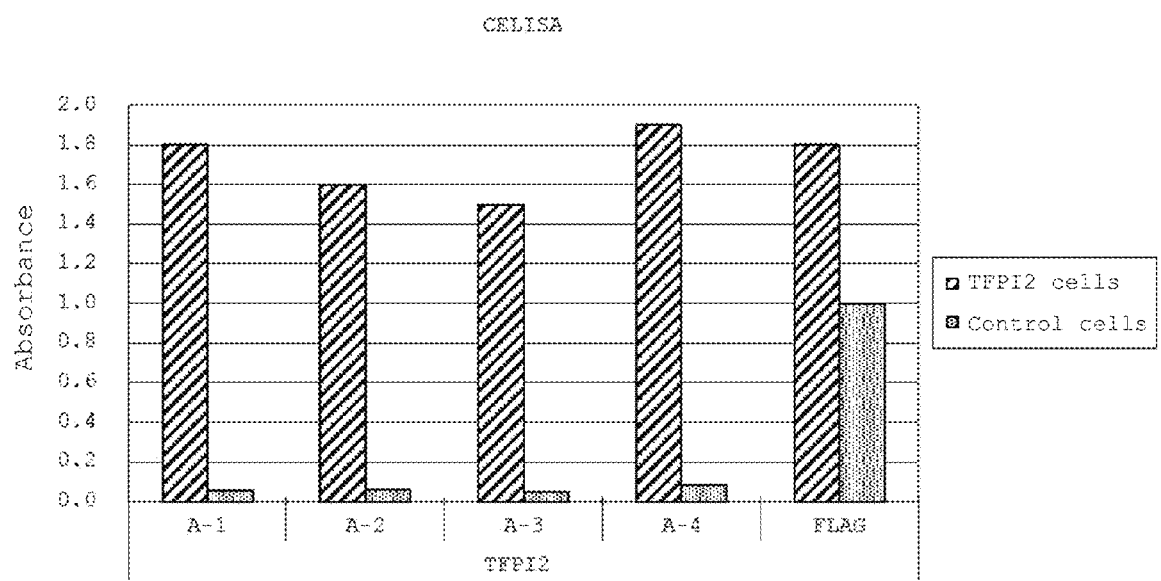
FIG. 4 is a diagram showing the results of measurement of the serum antibody titer in each mouse by CELISA analysis using GPI-anchor type TFPI2. The ordinate represents the absorbance.

The results of the CELISA analysis are shown in FIG. 4. In the negative control cells, signals could be hardly found for any of the antisera. In contrast, the TFPI2-expressing cells showed clear signals. From these results, it was shown that anti-TFPI2 antisera having high specificity could be obtained by the DNA immunization carried out in Example 2.

Figure 5:
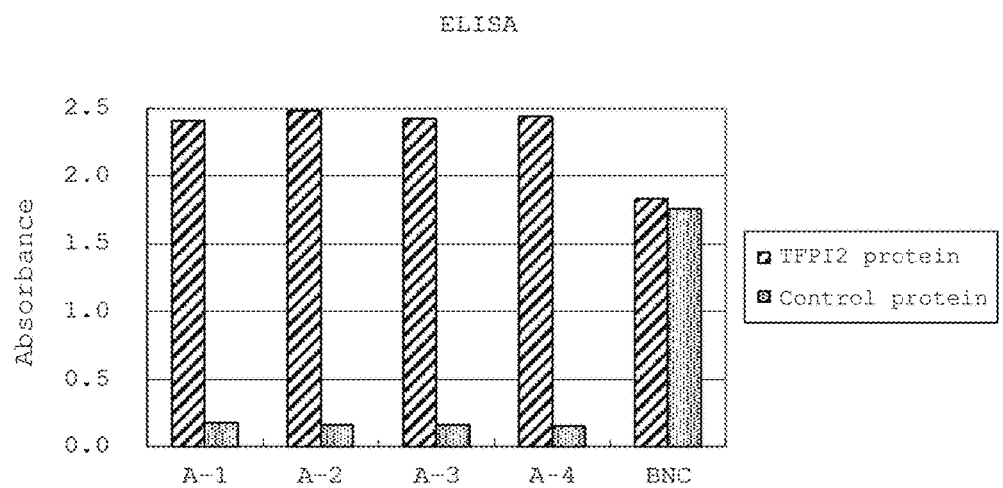
FIG. 5 is a diagram showing the results of measurement of the serum antibody titer in each mouse by ELISA analysis using secretory TFPI2. The ordinate represents the absorbance.

The results of the ELISA analysis are shown in FIG. 5. Similarly to the results of CELISA, when the antisera (A1 to A4) were used, clear signals were found only for TFPI2. Thus, this method also showed that antisera having high specificity could be obtained by the DNA immunization carried out in Example 2.

The results shown in FIG. 4 and FIG. 5 together indicate that the mouse antisera obtained in Example 2 are antisera having high specificity to both the GPI-anchor type TFPI2 and the secretory TFPI2.

<Example 6> Establishment of Hybridomas

Hybridomas capable of producing antibodies against TFPI2 were established by the following method.

(1) From mice in which an increase in the antibody titer due to the DNA immunization was found in Example 2, spleen cells were collected, and splenic cells were obtained therefrom.

(2) Cell fusion was carried out with the splenic cells collected and the mouse myeloma cell line SP2/0 in the presence of polyethylene glycol according to a conventional method.

(3) By culturing the resulting cells with HAT (manufactured by Sigma-Aldrich)/GIT medium (manufactured by Wako Pure Chemical Industries, Ltd.) for about 10 days, selection of antibody-producing cell hybridomas was carried out.

(4) Culture supernatants of the selected antibody-producing cell hybridomas were subjected to the CELISA described in Example 5 (1) and the ELISA described in Example 4 (A) to perform screening of hybridomas capable of producing antibodies against TFPI2.

(5) From the cells in the wells selected by the screening, monoclones were obtained by the limiting dilution method, and the monoclones were subjected to acclimation culture from HT (manufactured by Sigma-Aldrich)/GIT medium to GIT medium. Finally, 10 kinds of hybridomas (TS-TF01 to TS-TF10) were established.

<Example 7> Identification of Antigenic Determinants

The antigenic determinant of each antibody was identified using cells expressing variants of KD1, KD2, and KD3, which are Kunitz domains of TFPI2. The preparation method for plasmids that express the variants is described below concretely.

(1) Using the primers described in the following (c), (d), and (e), polynucleotides corresponding to the KD1 region, the KD2 region, or the region from KD3 to the C-terminus, of TFPI2 were amplified by RT-PCR according to a conventional method.

(c) Primers for GPI-Anchor Type TFPI2-KD1

```
Forward:
                                             (SEQ ID NO: 6
5'-cgatgacgacaagcttgctcaggagccaaca-3';
``` wherein the 15 bases in the 3'-end side correspond to the base sequence from position 73 to position 87 in GenBank No. NM_006528)

```
Reverse:
                                             (SEQ ID NO: 7
5'-catcagtggtgaattcttttctatcctcca-3';
``` wherein the 15 bases in the 5'-end side correspond to the base sequence from position 259 to position 273 in GenBank No. NM_006528)

(d) Primers for GPI-Anchor Type TFPI2-KD2

```
Forward:
                                             (SEQ ID NO: 8
5'-cgatgacgacaagcttgtcccaaagtttgc-3';
``` wherein the 15 bases in the 3'-end side correspond to the base sequence from position 274 to position 288 in GenBank No. NM_006528)

```
Reverse:
                                             (SEQ ID NO: 9
5'-catcagtggtgaattctttctttggtgcgca-3';
``` wherein the 15 bases in the 5'-end side correspond to the base sequence from position 445 to position 459 in GenBank No. NM_006528)

(e) Primers for GPI-Anchor Type TFPI2-KD3

```
Forward:
                                             (SEQ ID NO: 10
5'-cgatgacgacaagcttattccatcattttgc-3';
``` wherein the 15 bases in the 3'-end side correspond to the base sequence from position 460 to position 474 in GenBank No. NM_006528)

```
Reverse:
                                             (SEQ ID NO: 11
5'-catcagtggtgaattcaaattgcttcttccg-3';
``` wherein the 15 bases in the 5'-end side correspond to the base sequence from position 691 to position 705 in GenBank No. NM_006528)

(2) Three kinds of GPI-type TFPI2 expression plasmids were constructed by the method described in Example 1 (2).

(3) Transiently expressing cells for the three kinds of polypeptides were prepared by the method described in Example 3, and the antigenic determinants of the 10 kinds of monoclonal antibodies described in Example 6 were identified.

Table 1 shows the antigenic determinant of each antibody revealed from the result of FACS analysis.

TABLE 1

| | Antigen determinant | |
|---|---|---|
| | KD1 | KD3 |
| 1 | TS-TF01 | TS-TF05 |
| 2 | TS-TF02 | TS-TF06 |
| 3 | TS-TF03 | TS-TF07 |
| 4 | TS-TF04 | TS-TF08 |
| 5 | | TS-TF09 |
| 6 | | TS-TF10 |

Figure 6:
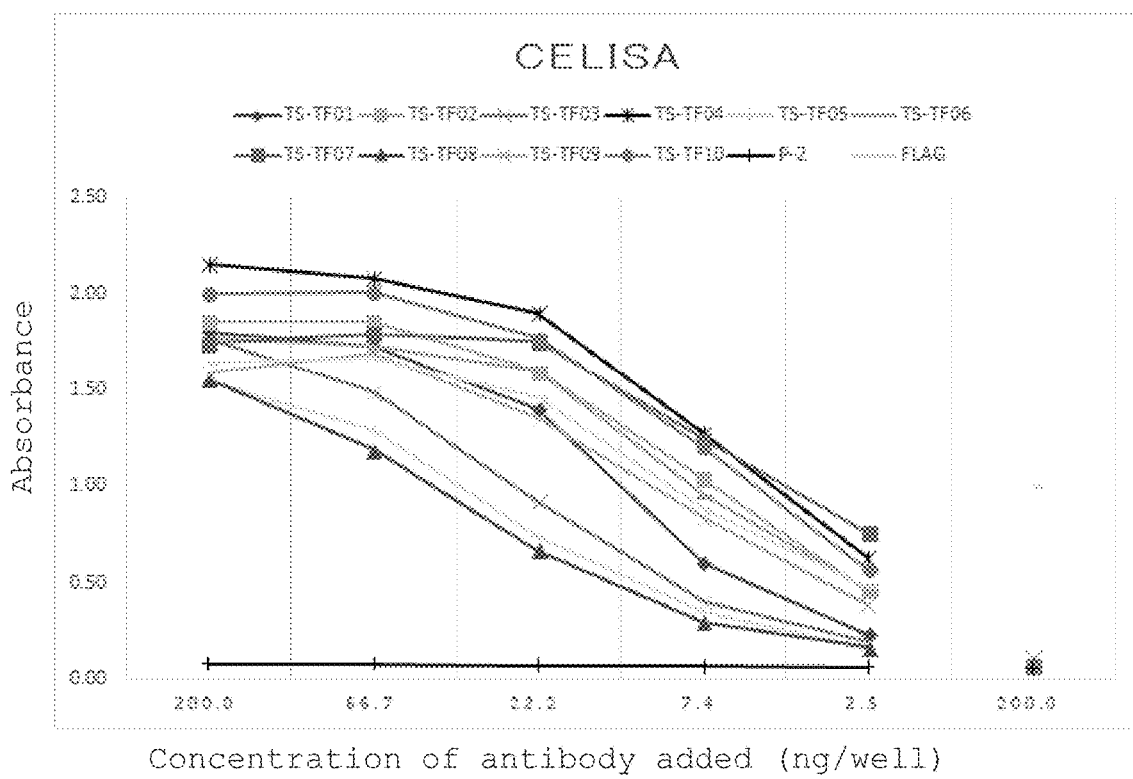
FIG. 6 is a diagram showing the results of analysis of each monoclonal antibody by CELISA analysis using GPI-anchor type TFPI2. The ordinate represents the absorbance, and the abscissa represents the concentration of the antibody added.

<Example 8> Preparation of Monoclonal Antibodies and CELISA Analysis Using Purified Antibodies From the 10 kinds of hybridomas established in Example 6, monoclonal antibodies against TFPI2 (anti-TFPI2 monoclonal antibodies) were prepared by the following method, and CELISA analysis was carried out.
(1) With 50% ammonium sulfate, 300 mL of the culture supernatant of each hybridoma established in Example 6 was fractionated, and the obtained fraction was dialyzed against TBS (Tris-Buffered Saline; 10 mM Tris-HCl+150 mM NaCl (pH 7.4)), followed by purification of a monoclonal antibody by the following method using HiTrap Protein G HP (manufactured by GE Healthcare).
(1-1) The column was preliminarily subjected to buffer replacement with PBS (Phosphate Buffer Saline; 10 mM phosphoric acid+150 mM NaCl (pH 7.4)), and the culture supernatant of the hybridoma was passed through the column at a flow rate of 10 mL/min.
(1-2) The column was sufficiently washed with 5 column volumes of PBS to remove unbound protein. In this process, by confirming that the absorbance at OD280 of the buffer that had passed through the column was not more than 0.01, unbound protein was judged not to be remaining.
(1-3) After washing the column, the bound antibody was eluted with an eluent (100 mM glycine (pH 2.5)). The eluted antibody was immediately neutralized by adding 1/10 volume of 1 M Tris (pH 8.0), and immediately subjected to dialysis with TBS, followed by quantification of the protein concentration of the purified antibody using an absorption spectrometer.
(2) From a mouse anti-FLAG M2 antibody (manufactured by SIGMA) as a positive control, an anti-TFPI2 P-2 antibody (manufactured by Santa Cruz) as a comparative control, and the above 10 kinds of anti-TFPI2 antibodies, antibody dilutions were prepared using 1% FBS/PBS solution such that the amount of each antibody added was 200 ng/well to 2.5 ng/well.
(2-1) The antibody dilutions were subjected to CELISA analysis by the method described in Example 5 (1). Only in the cases where the antibody was added at 200 ng/well, analysis was carried out for both the TFPI2-expressing cells and the control cells. In the cases where the antibody dilutions at not more than 66.6 ng/well were used, analysis was carried out only for TFPI2-expressing cells. The results of the CELISA analysis are shown in FIG. 6. The anti-FLAG antibody, which is a positive control, showed clear signals in both the TFPI2-expressing cells and the negative control cells. The anti-TFPI2 P-2 antibody, which is a comparative control, showed no signal in the TFPI2-expressing cells. Since this antibody is for use in WB, that is, for use in detection of denatured protein, it is very natural that no reactivity can be found in this analysis system, wherein TFPI2 having a naturally occurring higher-order structure is used. On the other hand, the above 10 kinds of anti-TFPI2 antibodies generally showed specific and concentration-dependent signals in the TFPI2-expressing cells although the signal varied among the antibodies.

<Example 9> Evaluation of Immunoprecipitability of Magnetic Beads on Which Monoclonal Antibodies are Immobilized Magnetic particles on which the 10 kinds of anti-TFPI2 monoclonal antibodies prepared in Example 8 are immobilized were prepared, and proteins in the culture supernatant of ovarian clear cell adenocarcinoma cells that specifically bind to the antibodies were identified by the following method. As the ovarian clear cell adenocarcinoma cells, three kinds of cells OVISE, OVMANA, and OVSAYO were used.
(1) Part of the purified monoclonal antibodies obtained in Example 8 were immobilized on Dynabeads M-280 Tosylactivated magnetic particles (manufactured by Invitrogen), and blocking was carried out with PBS supplemented with 0.5% BSA, to prepare antibody-immobilized magnetic particles.
(2) Immunoprecipitation-Western Blotting Method (IP-WB Method)
(2-1) The three kinds of cancer cells were cultured in RPMI 1640 medium (manufactured by Wako Pure Chemical Industries, Ltd.) supplemented with 10% fetal bovine serum at 100% confluence for three days.
(2-2) After centrifugation of the culture supernatant, each of the ten kinds of antibody-immobilized magnetic particles prepared by the method described in Example 8 were added to 0.1 mL of the supernatant, and the resulting mixture was stirred at room temperature for 1 hour to allow the reaction to proceed.
(2-3) The antibody-immobilized magnetic particles were washed twice with PBST-NP40 (0.1% Tween 20, 1% NP40), and then three times with PBS that does not contain a detergent.
(2-4) Proteins bound to each kind of antibody-immobilized magnetic particles were analyzed by the Western blotting described in Example 4 (B). As molecular weight markers, Full-Range Rainbow Molecular Weight Markers (manufactured by GE) were used. As the gel for the SDS-PAGE, a 10-20% gradient gel (manufactured by Marysol) was used. For the Western blotting, a detection antibody was prepared by labeling an anti-TFPI2 peptide antibody that recognizes the N-terminus of intact TFPI2 (see Non-patent Document 6) using an alkaline phosphatase labeling kit (manufactured by Dojindo Laboratories), which antibody was established by the department of gynecology, Yokohama City University. The detection was carried out by the method described in Example 4. The WB data was analyzed by Labo 1D software attached to Chemi-Stage (manufactured by Kurabo Industries Ltd.), wherein the signal intensities per unit area in A and B, where strong signals of the antibodies were found, were digitized. This study was carried out three times. The results of the areal Labo 1D software analysis were obtained by calculating the signal average and the standard error for the results of the three times of tests.

Figure 7:
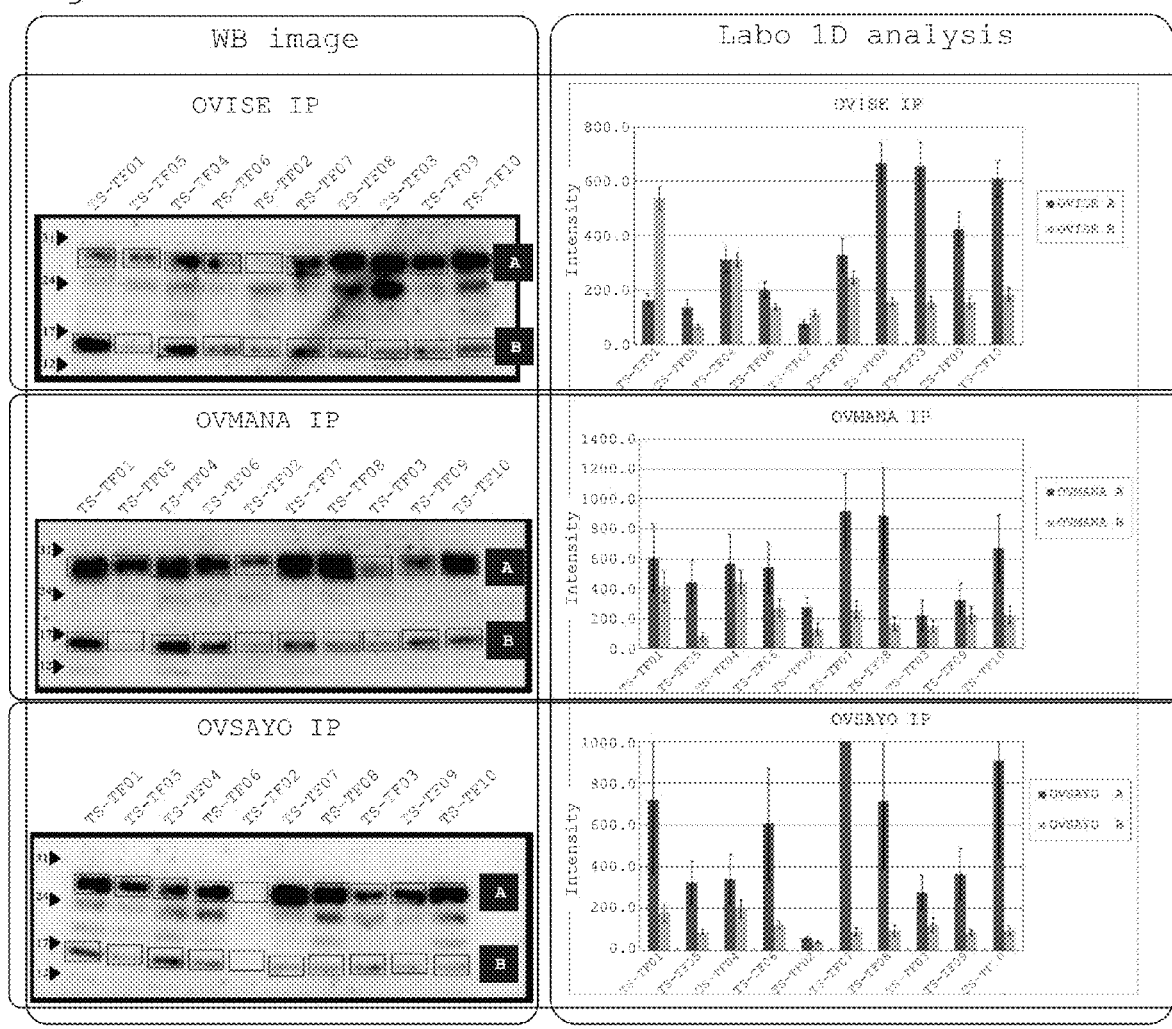
FIG. 7 is a diagram (photographs) showing the results of analysis of each monoclonal antibody by immunoprecipitation-Western blotting (IP-WB) analysis using culture supernatants of three kinds of ovarian cancer cells. The ordinate in each graph represents the signal intensity per unit area.

Images obtained by the analysis by the IP-WB method and the results of analysis of WB signals by the Labo 1D software are shown in FIG. 7. From the culture supernatant, clear signals were detected near a molecular weight of about 28,000 and near a molecular weight of about 16,000. Since an antibody that recognizes the N-terminus of TFPI2 is used in the WB analysis, the signal (A) near a molecular weight of about 28,000 was assumed to correspond to intact TFPI2, and the signal (B) near a molecular weight of about 16,000 was assumed to be a TFPI2 fragment polypeptide produced by reduction of the molecular weight for some reason. Its signal per unit area varied among the antibodies. The TS-TF01 antibody and the TS-TF04 antibody, which have antigenic determinants in Kunitz domain 1, tended to show high signals. This TFPI2 fragment polypeptide, which contains Kunitz domain 1, was provided as NT-TFPI2.

<Example 10> Identification of Monoclonal Antibody-Bound Proteins by Mass Spectrometry Further study by IP-WB was carried out using magnetic particles on which a total of three kinds of antibodies (the TS-TF01 antibody and the TS-TF04 antibody, which were found to have high affinity to NT-TFPI2 in Example 9, and the TS-TF05 antibody as a control) are immobilized. The NT-TFPI2 polypeptide, which binds to the TS-TF01 antibody and the TS-TF04 antibody, was analyzed by mass spectrometry. Using the culture supernatants of two kinds of ovarian cancer cells OVISE and OVMANA prepared in Example 9, IP-WB was carried out for samples prepared by the method described in Example 9. Only for the OVMANA sample, sample preparation for mass spectrometry was carried out as follows.
(1) The OVMANA sample solution was concentrated using an evaporator, and separated by SDS-PAGE was carried out. The separated proteins were stained by Ruby staining (manufactured by Invitrogen).
(2) Three kinds of stained fragments near a molecular weight of about 16,000 and one kind of unstained fragment in the vicinity (TS-TF01: fragments shown in A and B in Ruby staining in FIG. 8; TS-TF04: fragments shown in C and D in Ruby staining in FIG. 8), that is, a total of four fragments, were cut out, and subjected to reduction-alkylation using dithiothreitol and iodoacetamide, followed by carrying out in-gel digestion with trypsin.
(3) The peptide fragments produced by the trypsin digestion were separated by 1D nano-LC system (Ultimate 3000, manufactured by Thermo Fisher Scientific Inc.) using a C18 reverse-phase column, and MS/MS measurement was carried out using an LTQ Orbitrap mass spectrometer (manufactured by Thermo Fisher Scientific Inc.). The obtained data were analyzed using Protein Discoverer 1.3 (manufactured by Thermo Fisher Scientific Inc.), and proteins were identified by performing search against amino acid sequences in the Swiss-Prot database.

Figures 1, 8:
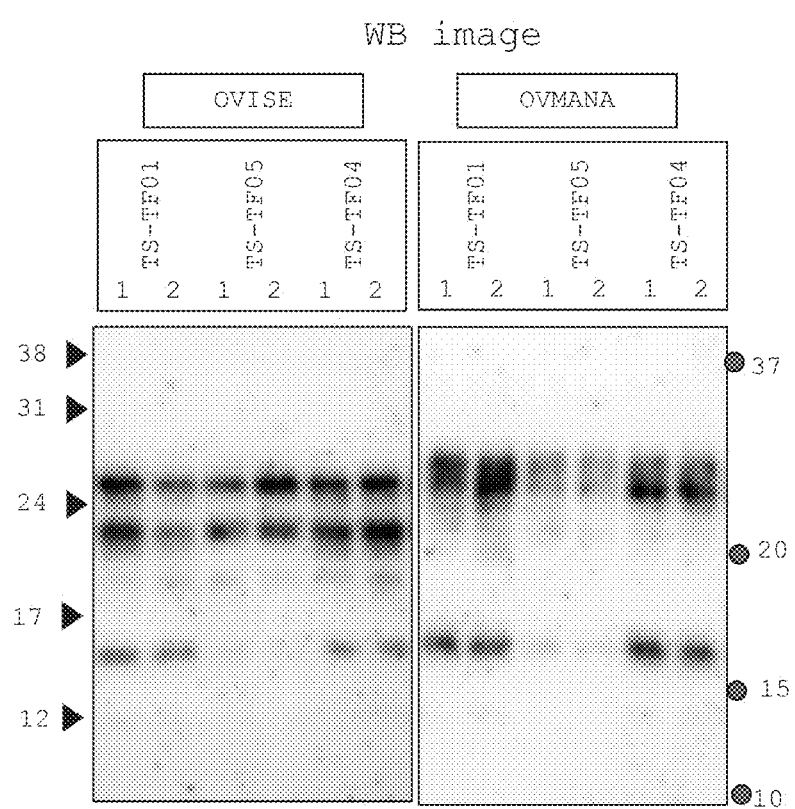
Figures 2, 8:
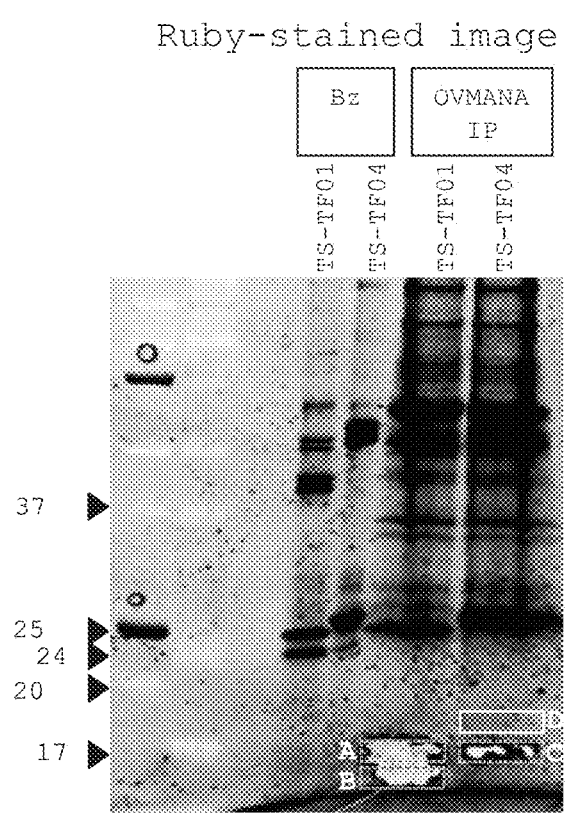

The proteins identified from the WB images and the Ruby-stained image, and from the IP products near a molecular weight of about 16,000, obtained from OVMANA, are shown in FIG. 8. In the WB images, clear signals that were assumed to be obtained from NT-TFPI2 were found near a molecular weight of about 16,000 for both TS-TF01 antibody and TS-TF04 antibody as well as for both OVISE and OVMANA. In the Ruby-stained image, the molecular weight of the clear band that was assumed to correspond to a TFPI2 fragment polypeptide having a decreased molecular weight seems to be slightly increased. This is, however, assumed to be due to disturbance of the electrophoresis due to influence of an increase in the salt concentration caused by sample concentration. From the mass spectrometry data of the OVMANA IP products, it was demonstrated that the total of three kinds of proteins A, B, and C near a molecular weight of about 16,000, whose staining could be clearly observed, are NT-TFPI2. From information on the C-terminal peptide identified (FF-SGGCH; SEQ ID NO:12) and the results obtained with the N-terminus-recognizing antibody, the NT-TFPI2 polypeptide was found to be a polypeptide containing at least the region from the 23rd aspartic acid to the 131st residue histidine in the amino acid sequence of the TFPI2 protein represented by SEQ ID NO:1.

In the present Example, the in-gel digestion was carried out using trypsin, which characteristically digests arginine and lysine residues. It can therefore be naturally thought that the polypeptide may contain a sequence that follows the 131st residue histidine in the C-terminal side of TFPI2 protein. That is, the present Example does not limit the sequence in the C-terminus of the NT-TFPI2 polypeptide.

<Example 11> Preparation of TFPI2 Assay Reagents

Since both intact TFPI2 and NT-TFPI2 were found to be present in the clear cell adenocarcinoma culture supernatants in Example 9 and Example 10, an "NT+I-TFPI2 assay system" assay reagent that comprehensively measures intact TFPI2 and NT-TFPI2 was prepared as follows using the TS-TF04 antibody, which has an antigenic determinant in Kunitz domain 1, in the solid-phase side, and the TS-TF01 antibody, which has an antigenic determinant in Kunitz domain 1, in the detection side. In addition, an "I-TFPI2 assay system" assay reagent that measures only intact TFPI2 was prepared as follows using the TS-TF04 antibody, which has an antigenic determinant in Kunitz domain 1, in the solid-phase side, and the TS-TF05 antibody, which has an antigenic determinant in Kunitz domain 3, in the detection side.
(1) Physical adsorption of an anti-TFPI2 monoclonal antibody (TS-TF04) to water-insoluble ferrite carriers was allowed at room temperature for one day and night such that the adsorption occurred at 100 ng/carrier, and blocking was then carried out with 100 mM Tris buffer (pH 8.0) supplemented with 1% BSA at 40° C. for 4 hours, to prepare anti-TFPI2 antibody-immobilized carriers.
(2) Two kinds of anti-TFPI2 labeled antibodies were prepared with anti-TFPI2 monoclonal antibodies (TS-TF01 and TS-TF05) using an alkaline phosphatase labeling kit (manufactured by Dojindo Laboratories).
(3) In each of magnetic force-permeable containers (volume, 1.2 mL), 12 antibody-immobilized carriers prepared in (1) were placed, and 50 µL of a buffer (Tris buffer supplemented with 3% BSA, pH 8.0) supplemented with 0.5 µg/mL of a labeled antibody prepared in (2) was added thereto, followed by carrying out freeze-drying, to prepare two kinds of TFPI2 assay reagents Assay Reagent A (NT+I-TFPI2 assay reagent using the TS-TF04 antibody/the TS-TF01 antibody) and Assay Reagent B (I-TFPI2 assay reagent using the TS-TF04 antibody/the TS-TF05 antibody). The TFPI2 assay reagents prepared were tightly closed and sealed under nitrogen gas, and stored at 4° C. until the assay.

<Example 12> Evaluation of Performances of TFPI2 Assay Reagents

Each 10-fold dilutions of the recombinant TFPI2 supernatant prepared in Example 4 and OVISE and OVMANA prepared in Example 9 in FBS were provided as samples containing TFPI2, and FBS alone was provided as a sample containing no TFPI2, to provide a total of four pseudosamples. The pseudosamples were used for evaluation of the two kinds of TFPI2 assay reagents prepared in Example 11, by five-point measurement.

As an evaluation device, a fully automatic enzyme immunoassay device AIA-1800 (manufactured by Tosoh Corporation; manufacturing/marketing notification number, 13B3X90002000002) was used. Measurement using the fully automatic enzyme immunoassay device AIA-1800 was carried out by:

(1) automatically dispensing 20 μL of a diluted sample and 80 μL of a diluent containing a surfactant to a container storing a TFPI2 assay reagent prepared in Example 11;
(2) carrying out antigen-antibody reaction at a constant temperature of 37° C. for 10 minutes;
(3) carrying out eight times of washing using a buffer containing a surfactant; and
(4) adding 4-methylumbelliferyl phosphate to the container. The concentration of 4-methylumbelliferone produced by alkaline phosphatase per unit time was provided as the measured value (nmol/(L·s)).

The measured values for the pseudosamples are shown in Table 2. Since any of the pseudosamples excluding FBS showed a coefficient of variation of not more than 3% in the five-point measurement, it was demonstrated that results obtained with the TFPI2 assay reagents prepared in Example 11 are reliable.

TABLE 2

| | Measured value [nmol/(L · s)] | | | |
|---|---|---|---|---|
| | FBS | Recombinant TFPI2 | OVISE | OVMANA |
| A) I + NT-TFPI2 | | | | |
| 1 | 0.09 | 230.25 | 33.09 | 112.22 |
| 2 | 0.08 | 233.26 | 34.59 | 112.34 |
| 3 | 0.09 | 236.27 | 33.35 | 111.87 |
| 4 | 0.10 | 229.63 | 34.44 | 113.27 |
| 5 | 0.10 | 224.61 | 35.09 | 114.93 |
| Average | 0.09 | 230.80 | 34.11 | 112.93 |
| SD | 0.01 | 4.36 | 0.85 | 1.23 |
| CV [%] | 7.28 | 1.89 | 2.50 | 1.09 |
| B) I-TFPI2 | | | | |
| 1 | 0.18 | 178.52 | 20.12 | 80.48 |
| 2 | 0.19 | 176.78 | 20.43 | 79.95 |
| 3 | 0.20 | 183.75 | 20.52 | 80.45 |
| 4 | 0.19 | 181.32 | 20.37 | 78.91 |
| 5 | 0.18 | 186.21 | 21.36 | 80.30 |
| Average | 0.19 | 181.32 | 20.56 | 80.02 |
| SD | 0.01 | 3.82 | 0.47 | 0.65 |
| CV [%] | 4.31 | 2.11 | 2.30 | 0.82 |

<Example 13> Study of TFPI2 Assay Reagents Using Culture Supernatant Panel for Various Ovarian Cancer Cells The present inventors, Arakawa et al., used a panel of cultured cells of various ovarian cancers including the clear cell type, serous type, and mucinous type, to carry out mass spectrometry of culture supernatants and real-time PCR analysis of gene expression in the cells. As a result, the present inventors identified TFPI2 as a molecule that is characteristically produced in the clear cell type (Patent Document 4). Therefore, if high measured values of TFPI2 are similarly observed only in culture supernatants of clear cell adenocarcinoma when the TFPI2 assay reagents described in Example 11 are used, the target of measurement by these reagents can be judged to be TFPI2. The culture supernatant panel for various ovarian cancer cells used by Arakawa et al. was analyzed with the TFPI2 assay reagents.

1) The following groups of cells were cultured in RPMI 1640 medium (manufactured by Wako Pure Chemical Industries, Ltd.) supplemented with 10% fetal bovine serum at 100% confluence for three days.
Clear cell type: OVISE, OVTOKO, OVMANA, OVSAYO
Serous type: OVKATE, OVSAHO
Mucinous type: RMUG-S, MCAS
2) By the method described in Example 12, a total of 8 kinds of culture supernatants were analyzed with the two kinds of TFPI2 assay reagents.

Figure 9:
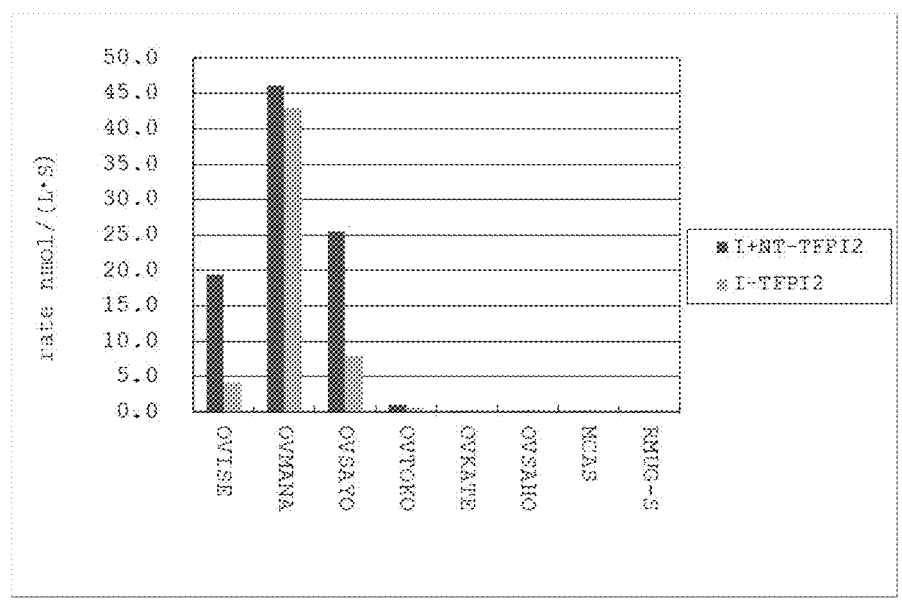
FIG. 9 is a diagram showing the results of analysis of culture supernatants of various ovarian cancers using two kinds of AIA assay reagents. "Rate" in the ordinate represents the amount of 4-methylumbelliferone produced per unit time [nmol/(L·s)].

The analysis results are shown in FIG. 9. In the cases of the clear cell type, all kinds of cells except OVTOKO showed high signals. On the other hand, the cells of the serous type and the mucinous type hardly showed signals. Very strong correlation was shown between the assay reagents. From these results, it was shown that TFPI2 is the target of measurement by the TFPI2 assay reagents.

<Example 14> Study of Molecular Weight of NT-TFPI2 Polypeptide by N-Glycanase Treatment From common databases such as UniProt, and known information from literatures and the like, TFPI2 is known to have asparagine-linked sugar chains attached to the asparagine residues at two positions 116 and 170 in the amino acid sequence of SEQ ID NO:1. Thus, from the results of Example 10, the NT-TFPI2 polypeptide was assumed to be a glycoprotein containing an asparagine-linked (N-type) sugar chain at the 116th residue. In view of this, changes in the molecular weight of the NT-TFPI2 polypeptide by sugar chain digestion treatment using N-glycanase were studied by carrying out IP-WB using the three kinds of antibodies described in Example 10, and the supernatants of OVISE, OVMANA, and OVSAYO described in Example 9 in the N-glycanase-treated group and the untreated group. At the same time, the IP efficiency of TFPI2 in each supernatant was analyzed by IP-AIA, wherein the calculation was carried out using the assay reagents prepared in Example 11.

(1) Two test groups each of which uses 400 μL each of supernatants of OVISE, OVMANA, and OVSAYO were provided. One of the test groups was used as an N-glycanase-treated group, wherein 1000 U PNGase F (manufactured by NEB) was added, and the other test group was used as an untreated group. In both test groups, incubated at 37° C. for 16 hours.
(2) For each antibody group, 100 μL of the supernatant treated in (1) was used. A control group in which magnetic particles alone were added and groups in which the three kinds of antibody-immobilized magnetic particles were added, that is, a total of four test groups, were provided. IP was carried out by the method described in Example 9. The solution after the reaction was separated into the supernatant fraction and the magnetic particle fraction using a magnet.
(3) The supernatant fraction was subjected to measurement using the two kinds of assay reagents described in Example 10. The influence of the N-glycanase treatment on the measured values of TFPI2, and the IP efficiencies of the three kinds of antibodies, were calculated. The calculation of the IP efficiency (recovery (%)) was carried out as follows: 100−(measured value for the supernatant described in (2)/ measured value for the reaction solution obtained with magnetic particles to which no antibody was bound).
(4) WB was carried out for the magnetic particle fraction by the method described in Example 9, and its luminescence signal was detected.

Figures 1, 10:
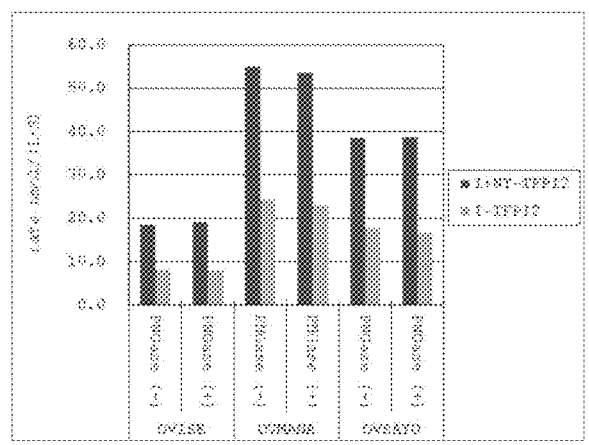
Figures 2, 10:
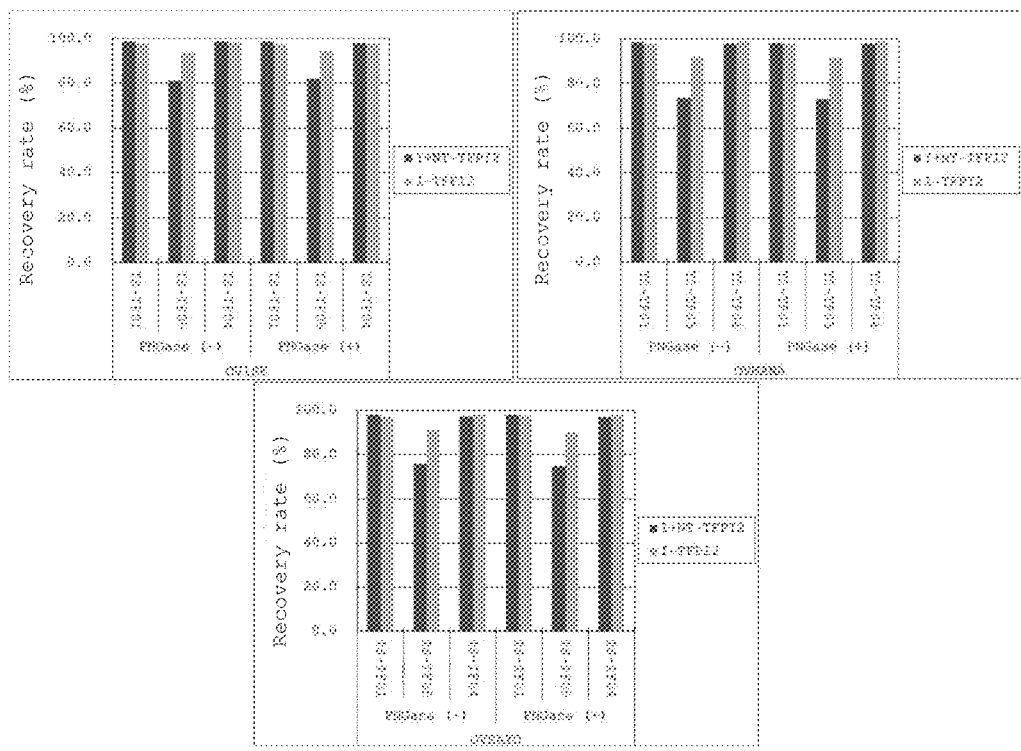
Figures 3, 10:
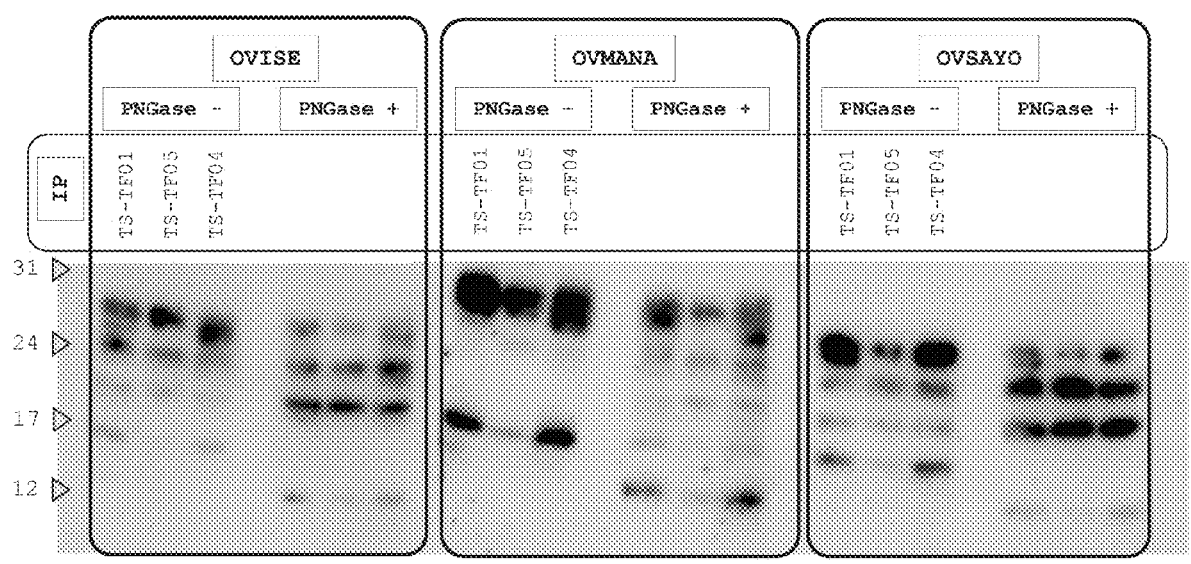

The influence of the N-glycanase treatment on the measured value of TFPI2, the IP recovery, and the WB images are shown in FIG. 10.

Whether or not the N-glycanase treatment was carried out did not cause changes in the measured value of TFPI2 and the IP efficiency. No inhibition of the reaction system by the N-glycanase treatment was found. In terms of the IP efficiency, the TS-TF04 and TS-TF01 IP groups showed recoveries of as high as not less than 97% in any of the results obtained using the three kinds of supernatants and the two kinds of assay systems. Thus, almost complete recovery of TFPI2 molecules was demonstrated. On the other hand, in the cases of TS-TF05 IP, a significant difference was found between A) the recovery by the NT+I-TFPI2 assay reagent, which was 74.3% in terms of the average calculated for four points, and B) the recovery by the I-TFPI2 reagent, which was 91.3% in terms of the average calculated for four points. It was suggested that region in TFPI2 recognized by TS-TF05 is different from those recognized by TS-TF04 and TS-TF01.

In terms of the WB results, in the cases where the N-glycanase treatment was not carried out, clear signals that were assumed to be obtained from the NT-TFPI2 polypeptide were found near a molecular weight of about 16,000 for both TS-TF01 antibody and TS-TF04 antibody as well as for all of the three kinds of culture supernatants. On the other hand, in the group in which the N-glycanase treatment was carried out, clear signals that were assumed to be obtained from the NT-TFPI2 polypeptide were found near a molecular weight of about 12,000 for all of the three kinds of culture supernatants. Since the signals that were assumed to be obtained from the NT-TFPI2 polypeptide, which has high affinity to the TS-TF01 antibody and the TS-TF04 antibody, clearly showed a decreased molecular weight due to the sugar chain digestion, it became clear that the NT-TFPI2 polypeptide has an N-type sugar chain modification.

<Example 15> Study of Temporal Changes in NT-TFPI2 Polypeptide

Figures 1, 11:
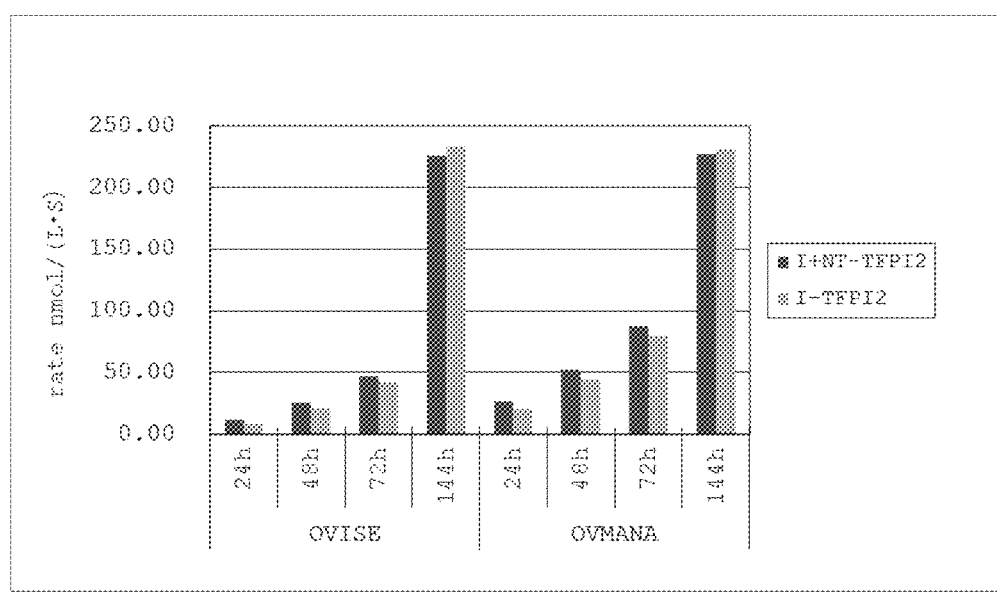
Figures 2, 11:
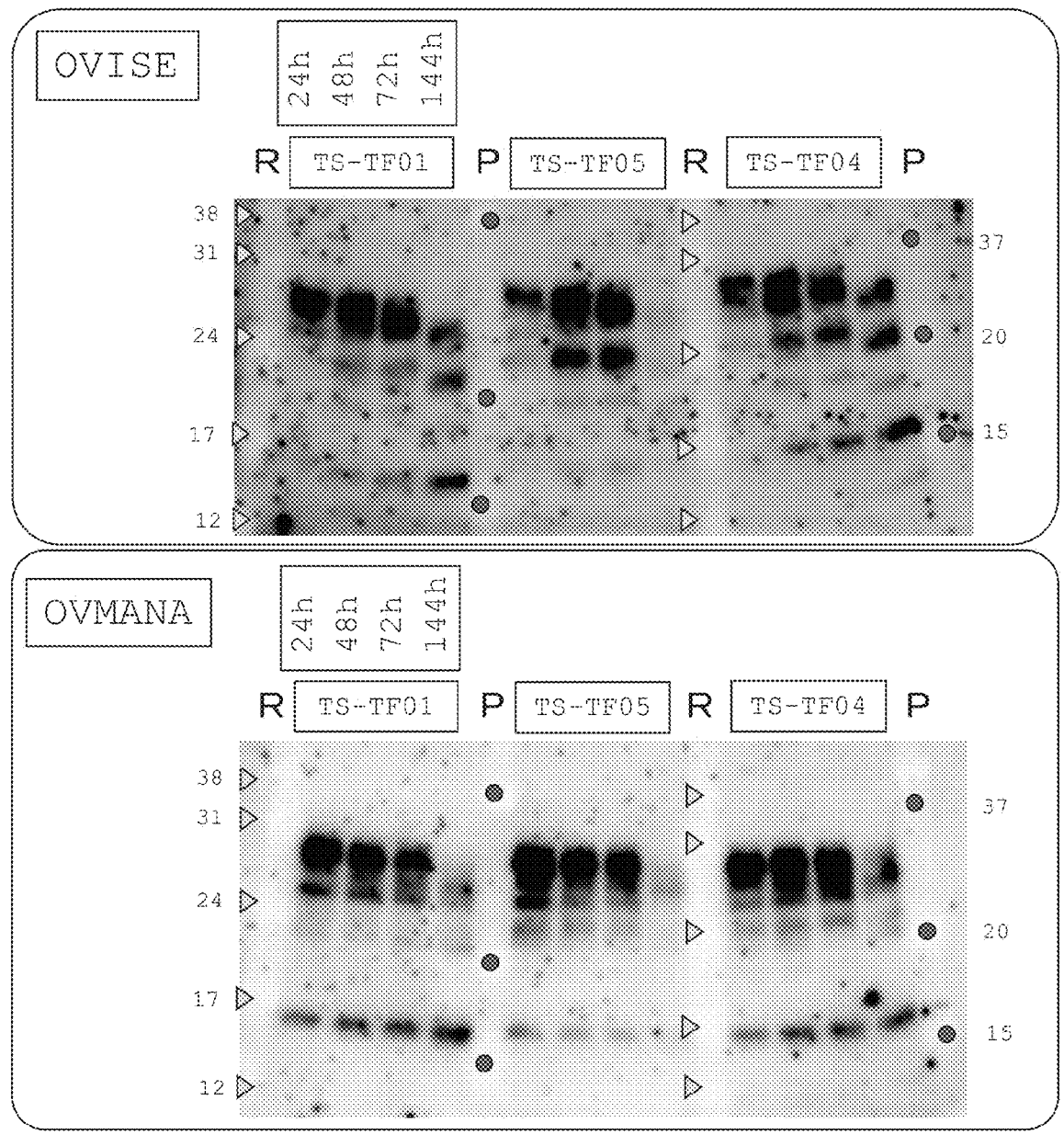

Aiming at elucidation of the mechanism of production of the NT-TFPI2 polypeptide, temporal changes of TFPI2 dynamics in a culture supernatant was analyzed by the IP-WB described in Example 9 or the IP-AIA method described in Example 14.
(1) OVISE, OVMANA, and OVSAYO cells were precultured in 15-cm dishes to confluence.
(2) To each dish, 20 mL of fresh medium was added, and the culture supernatant was collected after Hours 24, 48, 72, and 144 during the culture.
(3) The four supernatants collected in (2) were subjected to IP using 100 µL of each supernatant per antibody by the method described in Example 9. Each of the three kinds of solutions containing antibody-immobilized magnetic particles was separated into the supernatant fraction and the magnetic particle fraction using a magnet.
(4) The supernatant fraction was subjected to measurement using the two kinds of assay reagents described in Example 11, to measure changes in the TFPI2 level in the culture supernatant over time.
(5) Since TFPI2 increases over time during the culture period, the TFPI2 levels in the four kinds of supernatants collected at different times need to be averaged before carrying out WB. Thus, based on the measured value of TFPI2 in the culture supernatant at Hour 24 in (4), the three magnetic particle fractions collected thereafter were appropriately diluted to adjust the amount of TFPI2 to be added to each lane in the SDS-PAGE in order to carry out the WB described in Example 9. The measured values of TFPI2 in the culture supernatants collected over time and the WB images are shown in FIG. 11.

TFPI2 in the culture supernatant showed a tendency to increase over time in both the NT+I-TFPI2 assay system and the I-TFPI2 assay system. In the WB results, clear signals that were assumed to be obtained from NT-TFPI2 were found near a molecular weight of about 16,000 in the supernatants collected after 144 hours of the culture for both TS-TF01 antibody and TS-TF04 antibody as well as for the culture supernatants of both OVISE and OVMANA. It became clear that these signals were increased sequentially both OVISE and OVMANA, they are present after Hour 24 in OVMANA.

<Example 16> Study of Intracellular TFPI2 Molecules in Cancer Cells

Production of intact TFPI2 and the NT-TFPI2 polypeptide secreted to the culture supernatant was shown by Examples 13 and 14. It is, of course, thought that the molecules are also localized in the cells. In view of this, intracellular TFPI2 molecules in the cells were analyzed by the IP-WB method.
1) According to the method described in Example 13, OVISE, OVMANA, and OVSAYO were cultured as the clear cell type, and OVKATE and OVSAHO were cultured as the serous type.
2) As a cell lysis buffer, a solution of 2 M thiourea, 7 M urea, 3% CHAPS, and 1% Triton X-100 was prepared. The medium was removed from the cell culture plate, and the culture plate was then washed three times with PBS, followed by adding the cell lysis buffer to the culture plate.
3) The cells were dissociated using a cell scraper from the culture plate, and centrifugation was carried out at 15,000 rpm for 20 minutes. The resulting supernatant fraction was provided as a cell lysate.
4) Using the cell lysate, measurement by the two kinds of TFPI2 assay reagents described in Example 11 and IP-WB using the three kinds of antibodies described in Example 9 were carried out.

Figures 1, 12:
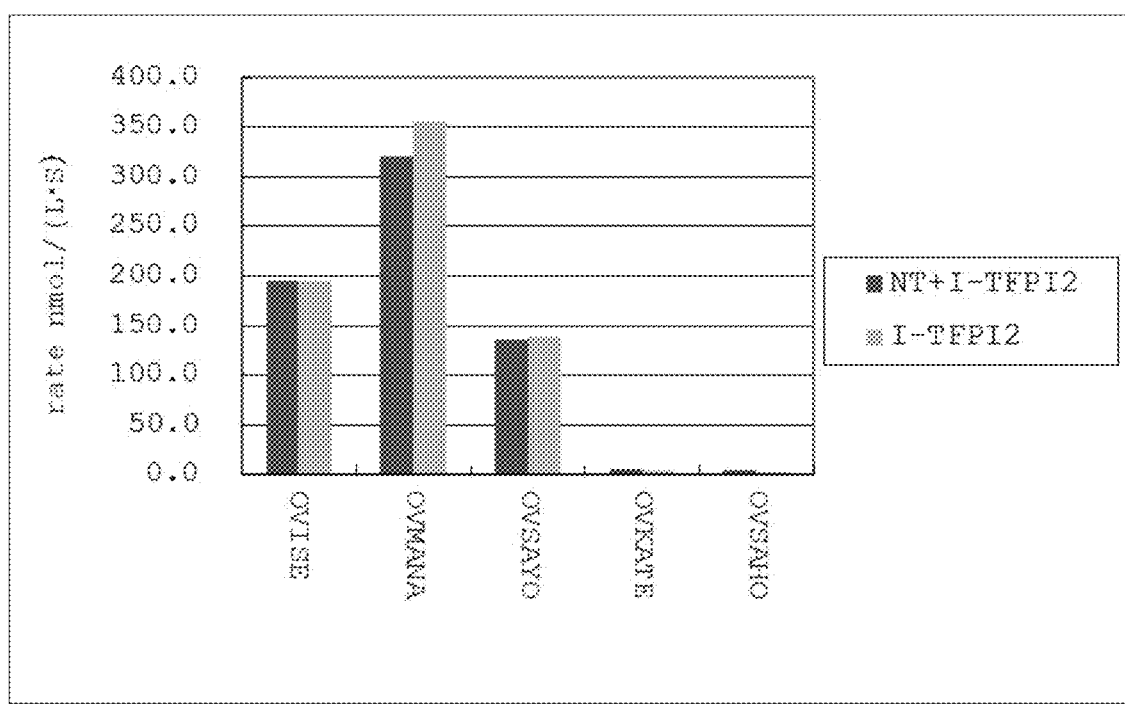
Figures 2, 12:
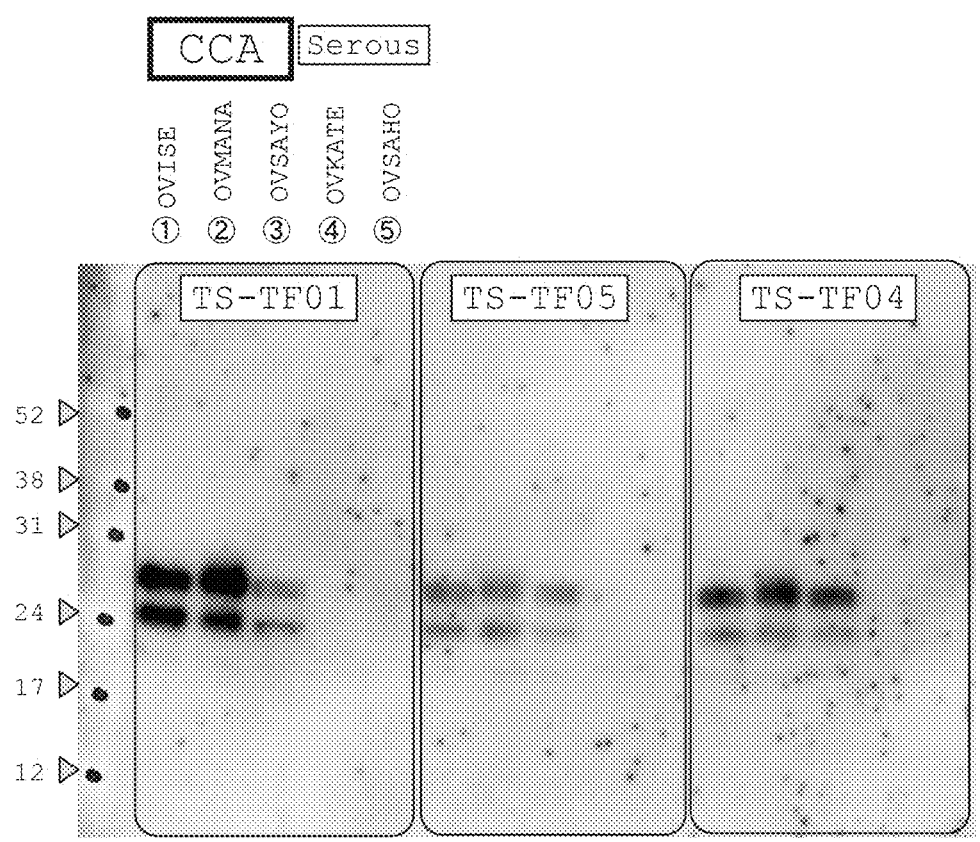

The analysis results obtained with the TFPI2 assay reagents and the WB images are shown in FIG. 12. Clear-cell-specific expression of TFPI2 was found in the cells as well as in the culture supernatant. In terms of the molecules in the cells, two clear signals were found between molecular weights of 24,000 and 31,000. Based on their molecular weights, the signals were assumed to be obtained from intact TFPI2 having a sugar chain, and intact TFPI2 having no sugar chain. On the other hand, the signal near a molecular weight of 16,000, which corresponds to NT-TFPI2, was lower than the detection limit. From these results, it was suggested that, while a large amount of intact TFPI2 molecules are present in the cells, whereas NT-TFPI2 may be present in the cells only in a small amount, or may be absent.

From Examples 14, 15, and 16, the NT-TFPI2 polypeptide was shown to be a glycoprotein produced by clear cell adenocarcinoma, to have an N-type sugar chain, and to be fractionated near a molecular weight of about 16,000. It was also shown that the NT-TFPI2 polypeptide is secreted to the culture supernatant and continuously accumulates therein, and that the NT-TFPI2 polypeptide is expressed only in a very small amount relative to intact TFPI2 in cancer cells, or is not expressed therein. In terms of the production mechanism, NT-TFPI2 is thought to be produced by undergoing processing for some reason after secretion.

<Example 17> Measurement of TFPI2 in Pregnancy Serum Samples

Sixty two pregnancy serum samples (samples purchased from ProMedDx) were used in the present Example. They were samples obtained during the period from the 5th week of pregnancy to the 40th week of pregnancy including the first trimester to the third trimester of pregnancy. All serum samples were obtained from Europeans and Americans with informed consent, according to description of the samples.

Using a fully automatic enzyme immunoassay device AIA-1800 (manufactured by Tosoh Corporation) as a device for the evaluation, measurement was carried out using the two kinds of assay reagents prepared in Example 11: the A) NT+I-TFPI2 assay reagent and the B) I-TFPI2 assay reagent.

Figure 13:
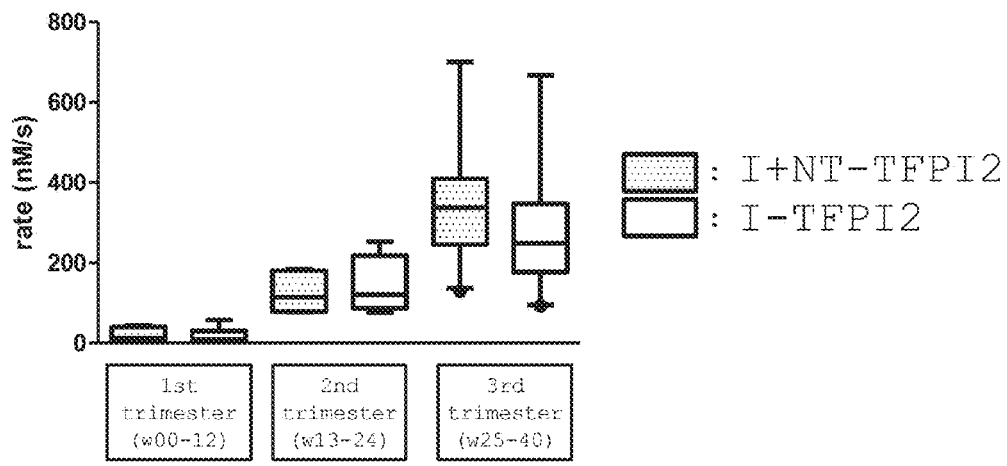
FIG. 13 is a diagram showing the results of AIA analysis on changes in TFPI2 over time during the gestation period.

A box plot of the measured values of TFPI2 is shown in FIG. 13. The minimum value, 25 percentile, median, 75 percentile, maximum value, and concentration range in the 95% confidence interval in each of the first, second, and third trimesters for each assay reagent are shown in Table 3. Since the measured values of TFPI2 showed strong correlation with the number of weeks of pregnancy and the blood level, the target of measurement by the two kinds of assay reagents prepared in Example 11 was detected TFPI2 in the serum samples.

TABLE 3

|  | TFPI2 | | | | | |
| --- | --- | --- | --- | --- | --- | --- |
|  | 1st trimester | | 2nd trimester | | 3rd trimester | |
|  | A) I + NT-TFPI2 | B) I-TFPI2 | A) I + NT-TFPI2 | B) I-TFPI2 | A) I + NT-TFPI2 | B) I-TFPI2 |
| Minimum value | 2.2 | 1.7 | 78.3 | 76.1 | 129.2 | 93.0 |
| 25 Percentile | 3.8 | 3.7 | 78.8 | 86.9 | 245.6 | 177.0 |
| Median | 12.3 | 9.6 | 115.1 | 121.2 | 337.7 | 249.1 |
| 75 Percentile | 40.2 | 30.2 | 180.7 | 218.5 | 409.4 | 348.0 |
| Maximum value | 44.0 | 58.4 | 184.6 | 252.2 | 700.0 | 667.0 |
| 95% Confidence interval | 1.3-33.6 | −1.2-36.8 | 74.2-176.2 | 70.6-218.9 | 304.4-387.9 | 235.7-311.1 |

<Example 18> Measurement of TFPI2 in Ovarian Cancer Samples

The sample panel (123 cases) used in the present Example is shown in Table 4. The samples are serum samples collected by the same protocol in the department of gynecology, Yokohama City University. The collection was carried out with informed consent and approval by the ethical committee of Yokohama City University.

TABLE 4

| <Sample panel content> | | | |
| --- | --- | --- | --- |
|  | | | Number of cases |
| Ovarian tumor | Benign | Mucinous | 15 |
|  |  | Teratoma | 15 |
|  |  | Serous | 5 |
|  |  | Fibrothecoma | 4 |
|  |  | Endometriosis | 13 |
|  |  | Other benign | 4 |
|  | Borderline malignant | Serous, mucinos | 7 |
|  | Malignant | Clear | 11 |

TABLE 4-continued

| <Sample panel content> | | | |
| --- | --- | --- | --- |
|  | | | Number of cases |
|  |  | Serous | 10 |
|  |  | Endometrioid | 7 |
|  |  | Mucinius | 5 |
|  |  | Other cancer | 9 |
| Uterine tumor | Benign | Uterine fibroids | 5 |
|  | Malignant | Cervical cancer | 8 |
|  |  | Endometrial cancer | 5 |
|  |  | Total | 123 |

Using a fully automatic enzyme immunoassay device AIA-1800 (manufactured by Tosoh Corporation) as a device for the evaluation, measurement was carried out using the two kinds of TFPI2 assay reagents prepared in Example 11 and a CA125 assay reagent (manufactured by Tosoh Corporation; approval number, 20700AMZ00504000).

Figure 14:
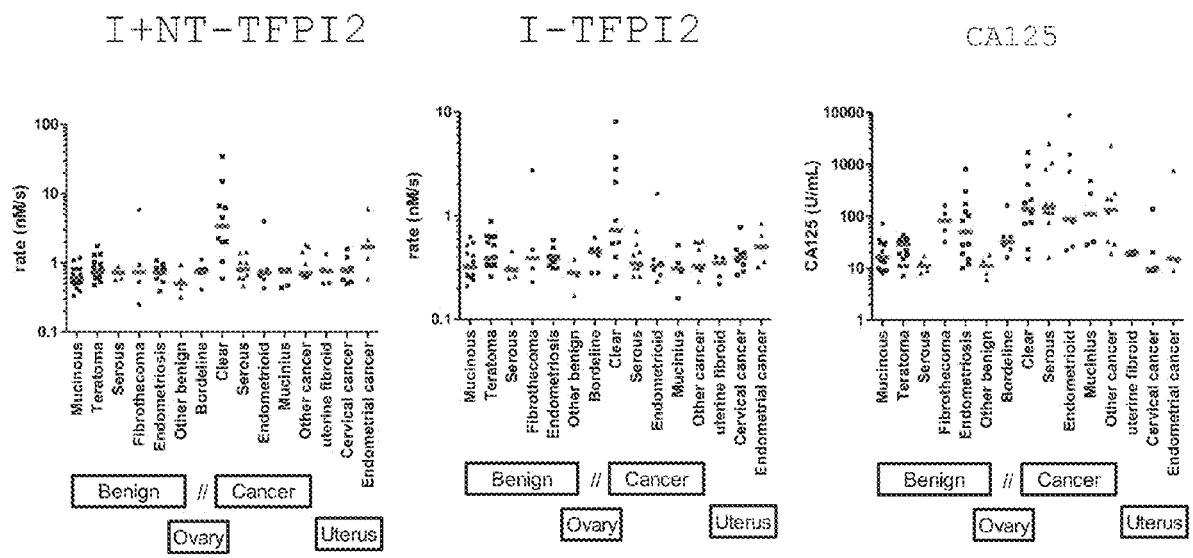
FIG. 14 is a diagram showing the results of AIA analysis of TFPI2 and CA125 in a panel for various gynecological tumors. Each horizontal line represents the median in each disease group.

The measured values of TFPI2 by the NT+I-TFPI2 assay system and the I-TFPI2 assay system, and the measured values of CA125 are shown in FIG. 14. CA125 tended to be at a high level generally in ovarian malignancies. The measured values by the NT+I-TFPI2 assay system and the I-TFPI2 assay system tended to be high in clear cell adenocarcinoma.

Figure 15:
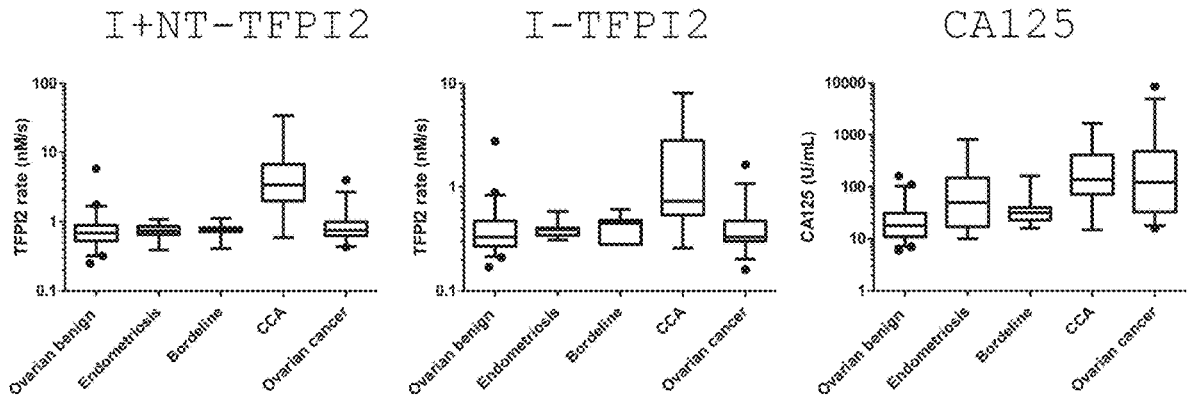
FIG. 15 is a diagram showing box plots of the measured values of TFPI2 and CA125 in a panel for various gynecological tumors.

The results of analysis of the panel were classified into those for five groups (benign ovarian tumor, endometriosis, borderline malignancy, clear cell adenocarcinoma, and other malignant ovarian tumors) as shown in FIG. 15. The minimum value, 25 percentile, median, 75 percentile, maximum value, and concentration range in the 95% confidence interval in each group for the measured values of the two kinds of TFPI2 and the measured values of CA125 are shown in Table 5. CA125 tended to be at a higher level in endometriosis than in benign ovarian tumor, and also tended to be clearly at a high level in malignant tumors in general. Since CA125 is an auxiliary marker for endometriosis, it is natural that it showed a high value in endometriosis among benign tumors. Since almost the same medians were obtained between clear cell adenocarcinoma and other malignant ovarian tumors, it can be said that CA125 cannot distinguish clear cell adenocarcinoma. On the other hand, the NT+I-TFPI2 assay system and the I-TFPI2 assay system tended to show a high measured value only in clear cell adenocarcinoma. It was also shown that the measured value by the NT+I-TFPI2 assay system tends to be higher.

TABLE 5

| | Ovarian benign | | | Endometriosis | | |
|---|---|---|---|---|---|---|
| | A) I + NT-TFPI2 | B) I-TFPI2 | CA125 | A) I + NT-TFPI2 | B) I-TFPI2 | CA125 |
| Minimum value | 0.25 | 0.17 | 6.00 | 0.39 | 0.31 | 10.00 |
| 25 Percentile | 0.53 | 0.27 | 11.00 | 0.65 | 0.35 | 17.00 |
| Median | 0.69 | 0.33 | 18.00 | 0.73 | 0.39 | 50.00 |
| 75 Percentile | 0.89 | 0.47 | 31.00 | 0.86 | 0.41 | 147.50 |
| Maximum value | 5.84 | 2.75 | 161.00 | 1.08 | 0.58 | 809.00 |
| 95% Confidence interval | 0.59-1.10 | 0.32-0.56 | 18.11-35.51 | 0.64-0.85 | 0.35-0.44 | 2.44-267.10 |

| | Borderline malignant | | | CCA | | | Ovarian cancer | | |
|---|---|---|---|---|---|---|---|---|---|
| | A) I + NT-TFPI2 | B) I-TFPI2 | CA125 | A) I + NT-TFPI2 | B) I-TFPI2 | CA125 | A) I + NT-TFPI2 | B) I-TFPI2 | CA125 |
| Minimum value | 0.41 | 0.28 | 16.00 | 0.59 | 0.25 | 15.00 | 0.43 | 0.16 | 16.00 |
| 25 Percentile | 0.72 | 0.32 | 23.00 | 1.99 | 0.54 | 72.00 | 0.63 | 0.30 | 33.00 |
| Median | 0.75 | 0.45 | 32.00 | 3.37 | 0.73 | 137.00 | 0.75 | 0.33 | 122.00 |
| 75 Percentile | 0.82 | 0.48 | 40.00 | 6.68 | 2.80 | 409.00 | 0.99 | 0.47 | 482.00 |
| Maximum value | 1.11 | 0.61 | 162.00 | 34.30 | 8.06 | 1691.00 | 3.97 | 1.63 | 8761.00 |
| 95% Confidence interval | 0.57-0.95 | 0.32-0.54 | 1.82-95.61 | 0.44-13.73 | 0.32-3.45 | 4.30-697.00 | 0.70-1.19 | 0.32-0.50 | 67.67-1264.00 |

Figure 16:
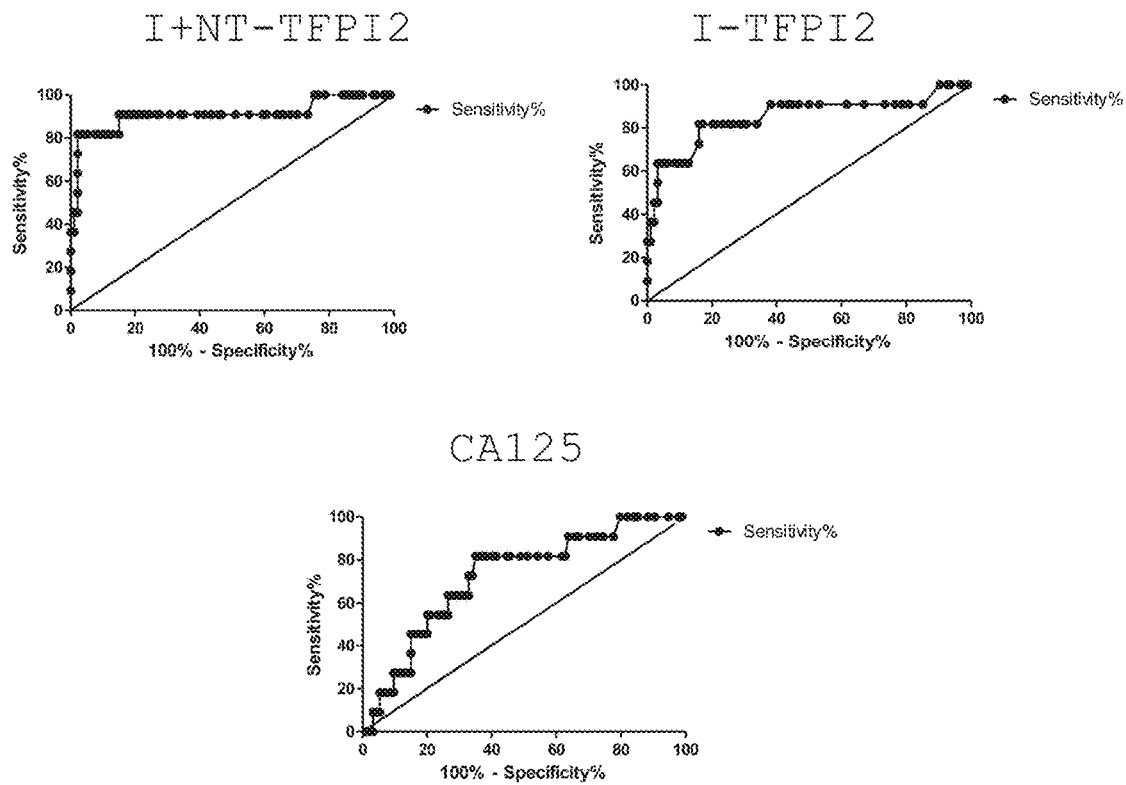
FIG. 16 is a diagram showing ROC curves of TFPI2 and CA125 for CCA and non-CCA ovarian tumor samples.

The results of the receiver operating characteristic (ROC) curve analysis of the data obtained by the NT+I-TFPI2 assay system, I-TFPI2 assay system, and CA125 measurement between the ovarian clear cell adenocarcinoma group and the other-ovarian-tumors group are shown in FIG. 16, and AUC (Area Under the Curve; area under the ROC curve) and the P-value in the significance test are shown in Table 6. The measured values of the two kinds of TFPI2 were significantly different between the ovarian clear cell adenocarcinoma group and the other-ovarian-tumors group with $p<0.0002$. Based on the statistical significance observed, it was shown that the two kinds of TFPI2 assay reagents are more useful for detection of ovarian clear cell adenocarcinoma than CA125. It was also shown that the NT+I-TFPI2 assay system, which comprehensively measures intact TFPI2 and NT-TFPI2, shows a better P-value and a better AUC than the I-TFPI2 assay system, which measures only intact TFPI2.

TABLE 6

| | A)I + NT-TFPI2 | B)I-TFPI2 | CA125 |
|---|---|---|---|
| Area under the curve (AUC) | 0.9101 | 0.8511 | 0.7234 |
| Standard error | 0.06454 | 0.0779 | 0.07529 |
| 95% Confidence interval | 0.7835 to 1.037 | 0.6983 to 1.004 | 0.5758 to 0.8710 |
| P-value | <0.0001 | 0.0001474 | 0.01568 |

Table 7 shows the sensitivity and the specificity between the ovarian clear cell adenocarcinoma group and the other-ovarian-tumors group as calculated by using the value obtained by the ROC analysis as the TFPI2 reference value (cutoff value) and using a value of 36 U/mL, which is close to a common reference value, as the CA125 reference value. Although the conditions were disadvantageous for CA125, usefulness of TFPI2 became clear at least from the viewpoint of specific diagnosis of clear cell adenocarcinoma. It was also shown that the A) NT+I-TFPI2 assay reagent has higher specificity than the B) I-TFPI2 assay reagent.

TABLE 7

| | A)I + NT-TFPI2 | B)I-TFPI2 | CA125 |
|---|---|---|---|
| Reference value | 1.91 | 0.54 | 36.0 U/mL |
| Sensitivity [%] | 81.82 | 81.82 | 81.82 |
| Specificity [%] | 97.87 | 84.04 | 58.51 |

Table 8 shows the positive rates for all clinical samples described in Example 17 as calculated by using the above reference value for TFPI2 and using 35 U/mL, which is a common reference value, for CA125. In this panel, the A) NT+I-TFPI2 assay reagent showed an extremely low false positivity, and allowed identification of clear cell adenocarcinoma with a high probability. Thus, the reagent was shown to have a sufficient performance as a diagnostic marker for clear cell adenocarcinoma.

TABLE 8

| | | | | NT + I-TFPI2 | | I-TFPI2 | | CA125 | |
|---|---|---|---|---|---|---|---|---|---|
| <Sample panel content> | | | Number of cases | Number of positive cases | Positive rate (%) | Number of positive cases | Positive rate (%) | Number of positive cases | Positive rate (%) |
| Ovarian tumor | Benign | Mucinous | 15 | 0 | 0.0 | 2 | 13.3 | 2 | 13.3 |
| | | Teratoma | 15 | 0 | 0.0 | 5 | 33.3 | 4 | 26.7 |
| | | Serous | 5 | 0 | 0.0 | 0 | 0.0 | 0 | 0.0 |
| | | Fibrothecoma | 4 | 1 | 25.0 | 1 | 25.0 | 3 | 75.0 |
| | | Endometriosis | 13 | 0 | 0.0 | 1 | 7.7 | 7 | 53.8 |
| | | Other benign | 4 | 0 | 0.0 | 0 | 0.0 | 0 | 0.0 |

TABLE 8-continued

|  |  |  |  | NT + I-TFPI2 | | I-TFPI2 | | CA125 | |
|---|---|---|---|---|---|---|---|---|---|
| | <Sample panel content> | | Number of cases | Number of positive cases | Positive rate (%) | Number of positive cases | Positive rate (%) | Number of positive cases | Positive rate (%) |
| | Borderline malignant | Serous, mucinos | 7 | 0 | 0.0 | 1 | 14.3 | 3 | 42.9 |
| | Malignant | Clear | 11 | 9 | 81.8 | 9 | 81.8 | 9 | 81.8 |
| | | Serous | 10 | 0 | 0.0 | 1 | 10.0 | 9 | 90.0 |
| | | Endometrioid | 7 | 1 | 14.3 | 1 | 14.3 | 5 | 71.4 |
| | | Mucinius | 5 | 0 | 0.0 | 0 | 0.0 | 3 | 60.0 |
| | | Other cancer | 9 | 0 | 0.0 | 3 | 33.3 | 6 | 66.7 |
| Uterine tumor | Benign | Uterine fibroids | 5 | 0 | 0.0 | 0 | 0.0 | 0 | 0.0 |
| | Malignant | Cervical cancer | 8 | 0 | 0.0 | 1 | 12.5 | 1 | 12.5 |
| | | Endometrial cancer | 5 | 2 | 40.0 | 2 | 40.0 | 1 | 20.0 |
| | | Total | 123 | | | | | | |

<Example 19> Sequence Analysis of C-Terminus of NT-TFPI2 Polypeptide by Mass Spectrometry The C-terminal sequence of the NT-TFPI2 polypeptide was analyzed by mass spectrometry using the heavy-oxygen water method.

Using the OVMANA prepared in Example 9 as an ovarian cancer cell culture supernatant, a sample for the mass spectrometry was prepared as follows using a TS-TF01 antibody column.
(1) Using a HiTrap NHS column (manufactured by GE Healthcare) and the TS-TF01 antibody, a TS-TF01 antibody-bound column was prepared according to a conventional method.
(2) Using a syringe, 10 mL of the OVMANA culture supernatant was passed through the antibody column three times, and washing was carried out with TBS three times.
(3) Through the antibody column, 1 mL of 0.1 M glycine (pH 2.0) solution was passed three times to collect an antibody column-bound fraction solution.
(4) The antibody column-bound fraction solution was concentrated with trichloroacetic acid, and developed by SDS-PAGE, followed by staining by SYPRO-Ruby staining (manufactured by Invitrogen).
(5) A total of three gel sections that were found to be stained (the sections #1 to #3 shown in the SYPRO-Ruby-stained image in FIG. 17A) were excised, and dehydrated with acetonitrile, followed by performing in-gel digestion using V8 protease (manufactured by SIGMA). In this step, in order to judge whether the obtained C-terminal sequence is produced by the in-gel digestion or by the action of processing by the cells based on the mass information, the in-gel digestion was carried out in 10 mM aqueous ammonium bicarbonate solution in which normal ultrapure water ($H_2O^{16}$) and heavy-oxygen water ($H_2O^{18}$) are mixed together at a ratio of 1:1.
(6) The resulting peptide digest was analyzed with a Triple TOF 5600 mass spectrometer (manufactured by AB Sciex) connected to a C18 reverse-phase nano-LC system. The measurement data were subjected to analysis using the Protein Pilot software (manufactured by AB Sciex), wherein the amino acid sequence was identified by performing search against amino acid sequences in the Swiss-Prot database.

FIG. 17A shows a SYPRO-Ruby-stained image of the antibody column-bound fraction; FIG. 17B shows the results of mapping of the sequence information identified from the bands #1 to #3 on the TFPI2 amino acid sequence; FIG. 17C shows mass spectra of precursor ions of representative TFPI2-derived peptides detected from the band #3; and Table 9 shows identification information of the corresponding ions. All of the bands of 28 kDa (#1), 24 kDa (#2), and 17.5 kDa (#3), which showed strong signals in the SYPRO-Ruby-stained image of the antibody column-bound fraction, were shown to correspond to the TFPI2 peptide. Among the peptides having a confidence value of not less than 99 and having a glutamic acid (E) or aspartic acid (D) residue immediately before the N-terminus (excluding 23DAAQEPTGNNAE34 (SEQ ID NO:13) immediately after the secretory signal sequence), 124KFFSGGCH131 (SEQ ID NO: 15) and 124KFFSGGC130 (SEQ ID NO:16) were detected only from #3. The seven sequences listed in Table 9, from top to bottom, correspond to SEQ ID NO: 13, SEQ ID NO: 13, SEQ ID NO: 14, SEQ ID NO: 14, SEQ ID NO: 15, SEQ ID NO: 16 and SEQ ID NO: 17, respectively.

TABLE 9

| Precursor ion molecular weight | Precursor ion m/z | Valency | Sequence | Modification | Confidence value | Theoretical molecular weight |
|---|---|---|---|---|---|---|
| 1215.50 | 608.76 | 2 | DAAQEPTGNNAE | No Label: 18O(1)@C-term | 99 | 1215.50 |
| 1217.51 | 609.76 | 2 | DAAQEPTGNNAE | Label: 18O(1)@C-term | 99 | 1217.50 |
| 1296.52 | 649.26 | 2 | ACDDACWRIE | Carbamidomethyl(C)@2, Carbamidomethyl(C)@6, Label: 18O(1)@C-term | 99 | 1296.51 |
| 1294.51 | 648.26 | 2 | ACDDACWRIE | Carbamidomethyl(C)@2, Carbamidomethyl(C)@6, No Label: 18O(1)@C-term | 99 | 1294.51 |
| 938.40 | 470.21 | 2 | KFFSGGCH | Carbamidomethyl(C)@7, No Label: 18O(1)@C-term | 99 | 938.41 |
| 801.35 | 401.68 | 2 | KFFSGGC | Carbamidomethyl(C)@7, No Label: 18O(1)@C-term | 99 | 801.35 |

TABLE 9-continued

| Precursor ion molecular weight | Precursor ion m/z | Valency | Sequence | Modification | Confidence value | Theoretical molecular weight |
|---|---|---|---|---|---|---|
| 1319.68 | 440.90 | 3 | DCKRACAKALK | Carbamidomethyl(C)@2, Carbamidomethyl(C)@6, No Label: 18O(1)@C-term | 99 | 1319.68 |

In the present Example, which aims at identification of the C-terminal sequence, an aqueous solution in which ultrapure water ($H_2O^{16}$) and heavy-oxygen water ($H_2O^{18}$) are mixed together at a ratio of 1:1 was used in the experiment system for the in-gel digestion using V8 protease. The peptides produced by the protease digestion in the gel are labeled with $O^{16}$ or $O^{18}$ almost to the same extent at their C-termini. In contrast, C-termini produced by the action of processing during the cell culture are not labeled with $O^{18}$.

For $_{23}$DAAQEPTGNNAE$_{34}$ (SEQ ID NO and $_{81}$ACD-DACWRIE$_{90}$ (SEQ ID NO:14), which were assumed to be internal peptides based on the representative examples of mass spectra of precursor ions of the peptides detected in the present Example (FIG. 17C) and the identification information of the corresponding ions (Table 9), peptides produced by labeling with $O^{18}$ at their C-termini and peptides produced normally with $O^{16}$ were simultaneously detected and identified. For example, as shown in FIG. 17C, monoisotopic ions of divalent ions corresponding to m/z 608.76 and m/z 609.76 labeled with $O^{16}$ and $O^{18}$ were detected for $_{23}$DAAQEPTGNNAE$_{34}$ (SEQ ID NO:13), and precursor ions were detected as a mixture of their corresponding isotopomers. A similar result was obtained for $_{81}$ACDDAC-WRIE$_{90}$ (SEQ ID NO:14). The above data indicate that these peptides are not positioned at the C-terminus, and demonstrate correctness of the present analysis system, which is intended for identification of the C-terminal sequence.

On the other hand, for $_{124}$KFFSGGCH$_{131}$ (SEQ ID NO:15), $_{124}$KFFSGGC$_{130}$ (SEQ ID NO:16), and $_{203}$DCK-RACAKALK$_{212}$ (SEQ ID NO:17), peptides produced with the $O^{16}$ label were detected and identified, but peptides produced with the $O^{18}$ label were not detected. It is thus strongly suggested that the C-terminal sequence of the NT-TFPI2 polypeptide is His131 or Cys130.

Taking into account the total results of the Examples of the present description, it is thought that the full-length TFPI2 detected in Western blotting correspond to Band #1 and Band #2; the N-terminus corresponds to Asp23; the C-terminus corresponds to Lys212; and the sequence after Lys212 is cleaved off for some reason. The difference in the mobility observed between Band #1 and Band #2 in SDS-PAGE may be due to a difference in the sugar chain structure of TFPI2. On the other hand, it became clear that the NT-TFPI2 polypeptide of 17.5 kDa detected by WB corresponds to Band #3, and that, although its N-terminus corresponds to Asp23 similarly to full-length TFPI2, its C-terminus corresponds to His 131 or Cys130.

Since $_{203}$DCKRACAKALK$_{212}$ (SEQ ID NO:17), which is positioned in the C-terminal side in full-length TFPI2, was also detected from Band #3, it is suggested that Band #3 includes not only NT-TFPI2, but also a polypeptide having a sequence positioned closer to the C-terminus relative to Arg132, that is, CT-TFPI2. However, since the C-terminal sequence of the NT-TFPI2 polypeptide was defined from mass information obtained by the heavy-oxygen water method, its validity is not deteriorated.

INDUSTRIAL APPLICABILITY

The present invention provides a novel detection marker for ovarian clear cell adenocarcinoma. The present invention also provides a method for detecting, with high sensitivity and specificity, only ovarian clear cell adenocarcinoma among benign ovarian tumors and malignant ovarian tumors having various tissue types. These are industrially very useful since they can be favorably applied to uses such as screening and postoperative follow-up of ovarian clear cell adenocarcinoma, and follow-up of endometriosis.

The invention claimed is:

1. A method for detecting ovarian clear cell adenocarcinoma, said method comprising measuring the amount of a processed tissue factor pathway inhibitor 2 (TFPI2) polypeptide in a sample,
   wherein the processed TFPI2 polypeptide has the following properties (i) to (iii):
   (i) a polypeptide having the amino acid sequence from the 23th residue aspartic acid to the 131st residue histidine or to the 130th residue cysteine in the TFPI2 amino acid sequence of SEQ ID NO:1, or a sequence having an identity of not less than 80% to this sequence;
   (ii) a polypeptide that is fractionated into a molecular weight of about 16,000 by reducing SDS-PAGE; and
   (iii) a polypeptide whose peptide fragment obtained after asparagine-linked sugar chain cleavage treatment is fractionated into a molecular weight of about 12,000 by reducing SDS-PAGE, and
wherein said measurement is performed by antigen-antibody reaction using an antibody that binds to an antigenic determinant in the region from the aspartic acid at position 23 to the histidine at position 131 or to the cysteine at position 130, in the amino acid sequence of SEQ ID NO: 1.

2. The method according to claim 1, further comprising measuring the amount of intact TFPI2 in said sample.

3. The method according to claim 2, wherein ovarian clear cell adenocarcinoma is judged to be detected in cases where the total of said amount of the processed TFPI2 polypeptide and said amount of intact TFPI2 exceeds a reference value calculated from a control.

4. The method according to claim 1, wherein said antibody is an antibody that recognizes Kunitz domain 1 of TFPI2.

* * * * *